(12) United States Patent
Hansen et al.

(10) Patent No.: US 7,846,697 B2
(45) Date of Patent: Dec. 7, 2010

(54) METHOD OF PRODUCING A LOW MOLECULAR WEIGHT ORGANIC COMPOUND IN A CELL

(75) Inventors: Joergen Hansen, Frederiksberg (DK); Thomas Hvid Andersen, Frederiksberg (DK); Finn Thyge Okkels, Roskilde (DK)

(73) Assignee: BLMaps, Frederiksberg C. (DK)

( * ) Notice: Subject to any disclaimer, the term of this patent is extended or adjusted under 35 U.S.C. 154(b) by 378 days.

(21) Appl. No.: 10/561,823

(22) PCT Filed: Jun. 14, 2004

(86) PCT No.: PCT/EP2004/051104

§ 371 (c)(1),
(2), (4) Date: Dec. 19, 2005

(87) PCT Pub. No.: WO2004/111254

PCT Pub. Date: Dec. 23, 2004

(65) Prior Publication Data

US 2006/0275877 A1 Dec. 7, 2006

(30) Foreign Application Priority Data

Jun. 19, 2003 (EP) .................................. 03101801
Aug. 26, 2003 (EP) .................................. 03102650

(51) Int. Cl.
*C12P 19/18* (2006.01)
*C12Q 1/68* (2006.01)
*G01N 33/53* (2006.01)

(52) U.S. Cl. .............................. 435/97; 435/6; 435/7.31
(58) Field of Classification Search ........................ None
See application file for complete search history.

(56) References Cited

U.S. PATENT DOCUMENTS

| 6,372,461 B1 | 4/2002 | Frost |
| 2006/0275877 A1 | 12/2006 | Hansen et al. |

FOREIGN PATENT DOCUMENTS

| FR | 2691880 A1 | 12/1993 |
| WO | WO01/07631 A2 | 2/2001 |
| WO | WO01/07631 A3 | 2/2001 |
| WO | WO 01/40491 A2 | 6/2001 |
| WO | WO 01/79520 A1 | 10/2001 |
| WO | WO 03/048375 A1 | 6/2003 |
| WO | WO 03/066836 A2 | 8/2003 |
| WO | WO03/066836 A2 | 8/2003 |
| WO | WO03/066836 A3 | 8/2003 |

OTHER PUBLICATIONS de Roode et al. Why are some alcohols easy to glucosylate with beta-glucosidases while others are not? A computational approach. J. Chem. Soc., Perkin Trans, 2: 2217-2224, 2000.*

Solanidine. www.rdchemicals.com.*
Moehs et al. oning and expression of solanidine UDP-glucose glucosyltransferase from potato. The Plant J. 11(2): 227-236, 1997.*
Priefert et al. Biotechnological production of vanillin. Applied Microbiol. Biotechnol 56:296-314, 2001.*
Arend et al. Utilizing genetically engineered bacteria to produce plant-specific glucosides. Biotechnol Bioeng. Sep. 2001;76(2):126-31.*
Overhage et al. Biotransformation of eugenol to vanillin by a mutant of *Pseudomonas* sp. strain HR199 constructed by disruption of the vanillin dehydrogenase ( vdh ) gene. Applied Micro. and Biotech. 52(6): 820-828, 1999.*
Quiros, L.M., et al.: "Two glycosyltransferases and a glycosidase are involved in oleandomycin modification during its biosynthesis by *Streptomyces antibioticus*", Molecular Microbiology, Blackwell Scientific, Oxford, GB, vol. 28, No. 6, Jun. 1998, pp. 1177-1185, XP000858900; ISSN: 0950-382X; p. 1181, right-hand column, paragraph 3—p. 1182, left-hand column, paragraph 1; figures 1, 7.
Raty, K. et al.: "A gene cluster from *Streptomyces galilaeus* involved in glycosylation of aclarubicin" Molecular and General Genetics, vol. 264, No. 1-2, Sep. 2000, pp. 164-172, XP002304279; ISSN: 0026-8925; abstract.
Sanchez, Cesar, et al.: "The biosynthetic gene cluster for the antitumor rebeccamycin: Characterization and generation of indolocarbazole derivatives" Chemistry and Biology (London), vol. 9, No. 4, Apr. 2002, pp. 519-531, XP002304280; ISSN: 1074-5521; abstract; figures 1,3,4.
Arana, Francisca E.: "Action of a beta-glucosidase in the curing of *Vanilla*" Food Research, ISSN: 0095-974X, vol. 8, 1943, pp. 343-351, XP009024054 p. 347, paragraph 3—p. 348, paragraph 1 p. 348, paragraph 3; table 2 p. 350, paragraph 4 abstract.
Zheng, Zuoxing, et al.: "Solid-State Bioconversion of Phenolics from Cranberry Pomace and Role of *Lentinus edodes*.beta.-Glucosidase" Journal of Agricultural and Food Chemistry, vol. 48, No. 3, Mar. 2000, pp. 895-900, XP002267398 abstract; figure 6; table 2 p. 898, col. 2, paragraph 2—p. 899, col. 1, paragraph 4.
Day, A. J., et al.: "Deglycosylation of flavonoid and isoflavonoid glycosides by human small intestine and liver beta-glucosidase activity" FEBS Letters, Elsevier Science Publishers, Amsterdam, NL, vol. 436, No. 1, Sep. 25, 1998, pp. 71-75, XP004258361 ISSN: 0014-5793 abstract; figure 1; table 1 p. 74, col. 1, paragraph 4.
Cicek, Muzaffer et al.: "The aglycone specificity-determining sites are different in 2,4-dihydroxy-7-methoxy-1,4-benzoxazin-3-one (DIMBOA)-glucosidase (maize.beta.-glucosidase) and dhurrinase (*Sorghum*.beta.-glucosidase)" Journal of Biological Chemistry, vol. 275, No. 26, Jun. 30, 2000, pp. 20002-20011, XP002267399 abstract; figure 1 p. 20002, col. 2, paragraph 2—p. 20003, col. 1, paragraph 1.

(Continued)

*Primary Examiner*—Michele K Joike
(74) *Attorney, Agent, or Firm*—Peter B. Scull; Kristina M. Kalan; Berenbaum Weinshienk PC

(57) ABSTRACT

A method of producing a low molecular weight organic compound (e.g. a plant or bacteria secondary metabolite) in increased yields involving use of a microorganism cell, which comprises a gene involved in the biosynthesis pathway leading to a low molecular weight organic aglycon compound and a glycosyltransferase gene capable of glycosylating the produced aglycon.

7 Claims, 1 Drawing Sheet

OTHER PUBLICATIONS

Figure 1:
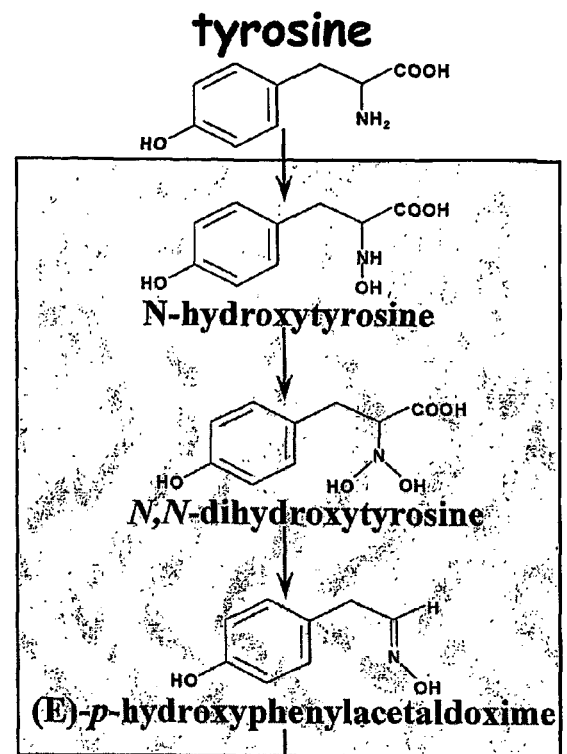
Figure 1:
Figure 1:

Bak, S. et al.: "Transgenic Tobacco and *Arabidopsis* Plants Expressing the Two Multifunctional *Sorghum* Cytochrome P450 Enzymes, CYP79A1 and CYP71E1, Are Cyanogenic and Accumulate Metabolites Derived From Intermediates in Dhurrin Biosynthesis" Plant Physiology, American Society of Plant Physiologists, Rockville, MD, US, vol. 123, Aug. 2000, pp. 1437-1448, XP001006399 ISSN: 0032-0889 cited in the application abstract; figure 1 p. 1440.

Tattersall, DB et al, "Resistance to an Herbivore Through Engineered Cyanogenic Glucoside Synthesis," Science; Sep. 7, 2001; vol. 293; pp. 1826-1828.

Rao, SR et al, "Review Vanilla flavour: production by conventional and biotechnological routes," Journal of the Science of Food and Agriculture; May 11, 2000; vol. 80, No. 3; pp. 289-304.

Paquette, S. et al, "On the origin of family 1 plant glycosyltransferases," Phytochemistry; Feb. 2003; vol. 62; pp. 399-413.

Hansen, EH et al, De Novo Biosynthesis of Vanillin in Fission Yeast (*Schizosaccharomyces pombe*) and Baker's Yeat (*Saccharomyces cerevisiae*), Applied and Environmental Microbiology; May 13, 2009; vol. 75, No. 9; pp. 2765-2774.

Nature Reviews, "In Brief: Industrial Microbiology," Nature Reviews Microbiology Report; May 2009; vol. 7, No. 5; p. 324.

Ehrenberg, R., "Yeast Bred to Bear Artificial Vanilla: Scientists co-opt fungi to produce flavor more efficiently," ScienceNews; May 23, 2009; vol. 176, No. 11.

Ehrenberg, R., "Yeast Bred to Bear Artificial Vanilla: Researchers have co-opted fungi to produce the flavor more efficiently," ScienceNews; http://www.sciencenews.org/view/generic/id/43124; May 23, 2009; vol. 176, No. 11.

* cited by examiner

SEQUENCE LISTING

```
<160> NUMBER OF SEQ ID NOS: 57

<210> SEQ ID NO 1
<211> LENGTH: 34
<212> TYPE: DNA
<213> ORGANISM: Artificial
<220> FEATURE:
<223> OTHER INFORMATION: PCR primer

<400> SEQUENCE: 1
attagaattc atgggcagca acgcgccgcc gccg                              34

<210> SEQ ID NO 2
<211> LENGTH: 34
<212> TYPE: DNA
<213> ORGANISM: Artificial
<220> FEATURE:
<223> OTHER INFORMATION: PCR Primer

<400> SEQUENCE: 2
attaaagctt ttactgcttg cccccgacca gcag                              34

<210> SEQ ID NO 3
<211> LENGTH: 28
<212> TYPE: DNA
<213> ORGANISM: Artificial
<220> FEATURE:
<223> OTHER INFORMATION: PCR Primer

<400> SEQUENCE: 3
caccatgggc agcaacgcgc cgccgccg                                     28

<210> SEQ ID NO 4
<211> LENGTH: 24
<212> TYPE: DNA
<213> ORGANISM: Artificial
<220> FEATURE:
<223> OTHER INFORMATION: PCR Primer

<400> SEQUENCE: 4
ttactgcttg cccccgacca gcag                                         24

<210> SEQ ID NO 5
<211> LENGTH: 21
<212> TYPE: DNA
<213> ORGANISM: Artificial
```

```
<220> FEATURE:
<223> OTHER INFORMATION: PCR Primer

<400> SEQUENCE: 5
atgaaagtga acgaggaaaa c                                              21

<210> SEQ ID NO 6
<211> LENGTH: 21
<212> TYPE: DNA
<213> ORGANISM: Artificial
<220> FEATURE:
<223> OTHER INFORMATION: PCR Primer

<400> SEQUENCE: 6
cgcagctgcc agggaggccg g                                              21

<210> SEQ ID NO 7
<211> LENGTH: 21
<212> TYPE: DNA
<213> ORGANISM: Artificial
<220> FEATURE:
<223> OTHER INFORMATION: PCR Primer

<400> SEQUENCE: 7
gcctccgccg gcctcgccgc c                                              21

<210> SEQ ID NO 8
<211> LENGTH: 21
<212> TYPE: DNA
<213> ORGANISM: Artificial
<220> FEATURE:
<223> OTHER INFORMATION: PCR Primer

<400> SEQUENCE: 8
cagaccacca actgcaggca g                                              21

<210> SEQ ID NO 9
<211> LENGTH: 21
<212> TYPE: DNA
<213> ORGANISM: Artificial
<220> FEATURE:
<223> OTHER INFORMATION: PCR Primer

<400> SEQUENCE: 9
gagagggaga ggccgtcgtc g                                              21

<210> SEQ ID NO 10
<211> LENGTH: 34
<212> TYPE: DNA
<213> ORGANISM: Artificial
<220> FEATURE:
<223> OTHER INFORMATION: PCR Primer

<400> SEQUENCE: 10
attagaattc atgaaagtga acgaagaaaa caac                                34

<210> SEQ ID NO 11
<211> LENGTH: 37
<212> TYPE: DNA
<213> ORGANISM: Artificial
<220> FEATURE:
<223> OTHER INFORMATION: PCR Primer

<400> SEQUENCE: 11
attaaagctt ttatttgttt agtcctaaac taacgac                             37
```

```
<210> SEQ ID NO 12
<211> LENGTH: 24
<212> TYPE: DNA
<213> ORGANISM: Artificial
<220> FEATURE:
<223> OTHER INFORMATION: PCR Primer

<400> SEQUENCE: 12
atgaaagtga acgaagaaaa caac                                         24

<210> SEQ ID NO 13
<211> LENGTH: 27
<212> TYPE: DNA
<213> ORGANISM: Artificial
<220> FEATURE:
<223> OTHER INFORMATION: PCR Primer

<400> SEQUENCE: 13
ttatttgttt agtcctaaac taacgac                                      27

<210> SEQ ID NO 14
<211> LENGTH: 21
<212> TYPE: DNA
<213> ORGANISM: Artificial
<220> FEATURE:
<223> OTHER INFORMATION: PCR Primer

<400> SEQUENCE: 14
atgaaagtga acgaggaaaa c                                            21

<210> SEQ ID NO 15
<211> LENGTH: 21
<212> TYPE: DNA
<213> ORGANISM: Artificial
<220> FEATURE:
<223> OTHER INFORMATION: PCR Primer

<400> SEQUENCE: 15
gaatccctcg tttcgatttc t                                            21

<210> SEQ ID NO 16
<211> LENGTH: 21
<212> TYPE: DNA
<213> ORGANISM: Artificial
<220> FEATURE:
<223> OTHER INFORMATION: PCR Primer

<400> SEQUENCE: 16
cttgacgcac gtgaggataa c                                            21

<210> SEQ ID NO 17
<211> LENGTH: 21
<212> TYPE: DNA
<213> ORGANISM: Artificial
<220> FEATURE:
<223> OTHER INFORMATION: PCR Primer

<400> SEQUENCE: 17
cctgacacgg tgcctgaccc g                                            21

<210> SEQ ID NO 18
<211> LENGTH: 21
<212> TYPE: DNA
<213> ORGANISM: Artificial
<220> FEATURE:
<223> OTHER INFORMATION: PCR Primer
```

<400> SEQUENCE: 18
cggaggggat tgaagggtgg g                                             21

<210> SEQ ID NO 19
<211> LENGTH: 31
<212> TYPE: DNA
<213> ORGANISM: Artificial
<220> FEATURE:
<223> OTHER INFORMATION: PCR Primer

<400> SEQUENCE: 19
attagaattc atggaacata ccccgcacat t                                  31

<210> SEQ ID NO 20
<211> LENGTH: 32
<212> TYPE: DNA
<213> ORGANISM: Artificial
<220> FEATURE:
<223> OTHER INFORMATION: PCR Primer

<400> SEQUENCE: 20
attagaattc ttatgtactg gaaattttgt tc                                 32

<210> SEQ ID NO 21
<211> LENGTH: 25
<212> TYPE: DNA
<213> ORGANISM: Artificial
<220> FEATURE:
<223> OTHER INFORMATION: PCR Primer

<400> SEQUENCE: 21
caccatggaa catccccgc acatt                                          25

<210> SEQ ID NO 22
<211> LENGTH: 22
<212> TYPE: DNA
<213> ORGANISM: Artificial
<220> FEATURE:
<223> OTHER INFORMATION: PCR Primer

<400> SEQUENCE: 22
ttatgtactg gaaattttgt tc                                            22

<210> SEQ ID NO 23
<211> LENGTH: 20
<212> TYPE: DNA
<213> ORGANISM: Artificial
<220> FEATURE:
<223> OTHER INFORMATION: PCR Primer

<400> SEQUENCE: 23
atggagcata cacctcacat                                               20

<210> SEQ ID NO 24
<211> LENGTH: 20
<212> TYPE: DNA
<213> ORGANISM: Artificial
<220> FEATURE:
<223> OTHER INFORMATION: PCR Primer

<400> SEQUENCE: 24
gacggccatg tgcctgtctc                                               20

<210> SEQ ID NO 25

```
<211> LENGTH: 20
<212> TYPE: DNA
<213> ORGANISM: Artificial
<220> FEATURE:
<223> OTHER INFORMATION: PCR Primer

<400> SEQUENCE: 25
ggggcagtct cccataatca                                            20

<210> SEQ ID NO 26
<211> LENGTH: 20
<212> TYPE: DNA
<213> ORGANISM: Artificial
<220> FEATURE:
<223> OTHER INFORMATION: PCR Primer

<400> SEQUENCE: 26
agggtcttaa agtggccctg                                            20

<210> SEQ ID NO 27
<211> LENGTH: 20
<212> TYPE: DNA
<213> ORGANISM: Artificial
<220> FEATURE:
<223> OTHER INFORMATION: PCR Primer

<400> SEQUENCE: 27
tacgggtctc tatcctaaca                                            20

<210> SEQ ID NO 28
<211> LENGTH: 32
<212> TYPE: DNA
<213> ORGANISM: Artificial
<220> FEATURE:
<223> OTHER INFORMATION: PCR Primer

<400> SEQUENCE: 28
attagaattc aaaaatcaca gggcagggaa ac                              32

<210> SEQ ID NO 29
<211> LENGTH: 41
<212> TYPE: DNA
<213> ORGANISM: Artificial
<220> FEATURE:
<223> OTHER INFORMATION: PCR Primer

<400> SEQUENCE: 29
attaggcgcg cctctagagt ctcttgtcct gtatcgtcgg g                    41

<210> SEQ ID NO 30
<211> LENGTH: 32
<212> TYPE: DNA
<213> ORGANISM: Artificial
<220> FEATURE:
<223> OTHER INFORMATION: PCR Primer

<400> SEQUENCE: 30
attagaattc tcagtataaa agagagccag ac                              32

<210> SEQ ID NO 31
<211> LENGTH: 40
<212> TYPE: DNA
<213> ORGANISM: Artificial
<220> FEATURE:
<223> OTHER INFORMATION: PCR Primer

<400> SEQUENCE: 31
```
attaggcgcg cctctagaga ctacctctga actttggaat        40

<210> SEQ ID NO 32
<211> LENGTH: 32
<212> TYPE: DNA
<213> ORGANISM: Artificial
<220> FEATURE:
<223> OTHER INFORMATION: PCR Primer

<400> SEQUENCE: 32
attagaattc ttgctcacat ctcactttaa tc                32

<210> SEQ ID NO 33
<211> LENGTH: 40
<212> TYPE: DNA
<213> ORGANISM: Artificial
<220> FEATURE:
<223> OTHER INFORMATION: PCR Primer

<400> SEQUENCE: 33
attaggcgcg cctctagaat attccaccag ctatttgtta        40

<210> SEQ ID NO 34
<211> LENGTH: 32
<212> TYPE: DNA
<213> ORGANISM: Artificial
<220> FEATURE:
<223> OTHER INFORMATION: PCR Primer

<400> SEQUENCE: 34
attagaattc caaaaagcaa agcctttgtg cc                32

<210> SEQ ID NO 35
<211> LENGTH: 40
<212> TYPE: DNA
<213> ORGANISM: Artificial
<220> FEATURE:
<223> OTHER INFORMATION: PCR Primer

<400> SEQUENCE: 35
attaggcgcg cctctagatt taattctcca cgcttataag        40

<210> SEQ ID NO 36
<211> LENGTH: 41
<212> TYPE: DNA
<213> ORGANISM: Artificial
<220> FEATURE:
<223> OTHER INFORMATION: PCR Primer

<400> SEQUENCE: 36
attaggcgcg ccggatcctt tcttgcgtta ttttcggcac c        41

<210> SEQ ID NO 37
<211> LENGTH: 32
<212> TYPE: DNA
<213> ORGANISM: Artificial
<220> FEATURE:
<223> OTHER INFORMATION: PCR Primer

<400> SEQUENCE: 37
attaaagctt gaaaaccgc cagccaggct tt                 32

<210> SEQ ID NO 38
<211> LENGTH: 34
<212> TYPE: DNA

<210> SEQ ID NO 39
<211> LENGTH: 34
<212> TYPE: DNA
<213> ORGANISM: Artificial
<220> FEATURE:
<223> OTHER INFORMATION: PCR Primer

<400> SEQUENCE: 38
attatctaga atgggcagca acgcgccgcc gccg            34

<210> SEQ ID NO 39
<211> LENGTH: 34
<212> TYPE: DNA
<213> ORGANISM: Artificial
<220> FEATURE:
<223> OTHER INFORMATION: PCR Primer

<400> SEQUENCE: 39
attaggatcc ttactgcttg cccccgacca gcag            34

<210> SEQ ID NO 40
<211> LENGTH: 34
<212> TYPE: DNA
<213> ORGANISM: Artificial
<220> FEATURE:
<223> OTHER INFORMATION: PCR Primer

<400> SEQUENCE: 40
attatctaga atgaaagtga acgaagaaaa caac            34

<210> SEQ ID NO 41
<211> LENGTH: 35
<212> TYPE: DNA
<213> ORGANISM: Artificial
<220> FEATURE:
<223> OTHER INFORMATION: PCR Primer

<400> SEQUENCE: 41
attaggatcc ttaccaccgt tctatctcca tcttc            35

<210> SEQ ID NO 42
<211> LENGTH: 31
<212> TYPE: DNA
<213> ORGANISM: Artificial
<220> FEATURE:
<223> OTHER INFORMATION: PCR Primer

<400> SEQUENCE: 42
attatctaga atggaacata ccccgcacat t               31

<210> SEQ ID NO 43
<211> LENGTH: 32
<212> TYPE: DNA
<213> ORGANISM: Artificial
<220> FEATURE:
<223> OTHER INFORMATION: PCR Primer

<400> SEQUENCE: 43
attaggatcc ttatgtactg gaaattttgt tc              32

<210> SEQ ID NO 44
<211> LENGTH: 34
<212> TYPE: DNA
<213> ORGANISM: Artificial
<220> FEATURE:
<223> OTHER INFORMATION: Primer

<400> SEQUENCE: 44
attatctaga atgggttcca ccggcgagac tcag            34

<210> SEQ ID NO 45
<211> LENGTH: 35
<212> TYPE: DNA
<213> ORGANISM: Artificial
<220> FEATURE:
<223> OTHER INFORMATION: Primer

<400> SEQUENCE: 45
attaggatcc tcagatcttc ttaagaaact caatg                          35

<210> SEQ ID NO 46
<211> LENGTH: 36
<212> TYPE: DNA
<213> ORGANISM: Artificial
<220> FEATURE:
<223> OTHER INFORMATION: Primer

<400> SEQUENCE: 46
attatctaga atgccttcca aactcgccat cacttc                         36

<210> SEQ ID NO 47
<211> LENGTH: 34
<212> TYPE: DNA
<213> ORGANISM: Artificial
<220> FEATURE:
<223> OTHER INFORMATION: Primer

<400> SEQUENCE: 47
attaggatcc ttacaaagcc gctgacagcg acag                           34

<210> SEQ ID NO 48
<211> LENGTH: 31
<212> TYPE: DNA
<213> ORGANISM: Artificial
<220> FEATURE:
<223> OTHER INFORMATION: Primer

<400> SEQUENCE: 48
attatctaga atggaacata cacctcacat t                              31

<210> SEQ ID NO 49
<211> LENGTH: 32
<212> TYPE: DNA
<213> ORGANISM: Artificial
<220> FEATURE:
<223> OTHER INFORMATION: Primer

<400> SEQUENCE: 49
attaggatcc ttatgtactg gaaattttgt tc                             32

<210> SEQ ID NO 50
<211> LENGTH: 34
<212> TYPE: DNA
<213> ORGANISM: Artificial
<220> FEATURE:
<223> OTHER INFORMATION: Primer

<400> SEQUENCE: 50
attatctaga atgaaagtta acgaagaaaa caac                           34

<210> SEQ ID NO 51
<211> LENGTH: 35
<212> TYPE: DNA
<213> ORGANISM: Artificial
<220> FEATURE:

<223> OTHER INFORMATION: Primer

<400> SEQUENCE: 51
attaggatcc ttaccaccgt tctatctcca tcttc                                35

<210> SEQ ID NO 52
<211> LENGTH: 33
<212> TYPE: DNA
<213> ORGANISM: Artificial
<220> FEATURE:
<223> OTHER INFORMATION: Primer

<400> SEQUENCE: 52
agcactagta tggcgacaat ggaggtagag gcc                                  33

<210> SEQ ID NO 53
<211> LENGTH: 34
<212> TYPE: DNA
<213> ORGANISM: Artificial
<220> FEATURE:
<223> OTHER INFORMATION: Primer

<400> SEQUENCE: 53
agcgaattct cagatggaga tggacgggta gagg                                 34

<210> SEQ ID NO 54
<211> LENGTH: 37
<212> TYPE: DNA
<213> ORGANISM: Artificial
<220> FEATURE:
<223> OTHER INFORMATION: Primer

<400> SEQUENCE: 54
agcactagta tggccaccac cgccaccccg cagctcc                              37

<210> SEQ ID NO 55
<211> LENGTH: 38
<212> TYPE: DNA
<213> ORGANISM: Artificial
<220> FEATURE:
<223> OTHER INFORMATION: Primer

<400> SEQUENCE: 55
agcgaattcc taggcggcgc ggcggttctt gtatttgg                             38

<210> SEQ ID NO 56
<211> LENGTH: 34
<212> TYPE: DNA
<213> ORGANISM: Artificial
<220> FEATURE:
<223> OTHER INFORMATION: Primer

<400> SEQUENCE: 56
agcgaattct cactgcttgc ccccgaccag cagc                                 34

<210> SEQ ID NO 57
<211> LENGTH: 32
<212> TYPE: DNA
<213> ORGANISM: Artificial
<220> FEATURE:
<223> OTHER INFORMATION: Primer

<400> SEQUENCE: 57
agcactagta tgggcagcaa cgcgccgcct cc                                   32

US 7,846,697 B2

METHOD OF PRODUCING A LOW MOLECULAR WEIGHT ORGANIC COMPOUND IN A CELL

FIELD OF THE INVENTION

The present invention relates to a method of producing a low molecular weight organic compound (e.g. a plant or bacteria secondary metabolite) in increased yields involving use of a cell (e.g. a plant or microorganism cell), which comprises a gene involved in the biosynthesis pathway leading to a low molecular weight organic aglycon compound and a glycosyltransferase gene capable of glycosylating the produced aglycon.

BACKGROUND OF THE INVENTION

Plants and microbes synthesize a large number of natural substances, in particular secondary metabolites, with diverse and generally unclear function. In contrast to the primary metabolites (e.g. amino acids, sugars, fatty acids), which are involved in fundamental functions like metabolism, growth, maintenance and survival, secondary metabolites are not required for fundamental functions. Many secondary metabolites from plants are known to act as repellants or natural pesticides in defense against herbivore animals or as sexual attractants to pollinating insects (Grisebach, 1988, In: European Conference on Biotechnology, Scientific, technical and industrial challenges, Verona, Italy, 7-8 Nov. 1988, pages 23-27), whereas fungal secondary metabolites often act as phytotoxins (Osbourn, 2001, Proceedings of the National Academy of the USA 98: 14187-14188).

Various secondary metabolites from more than 100 different plant species have been shown to exert antimicrobial activity (Cowan, 1999, Clinical Microbiology Reviews 12: 564-582) and a large number of secondary metabolites from common food plants are not only responsible for the taste and color but are also believed to have health promoting activities (Eastwood, 2001, Quarterly Journal of Medicine 94: 45-48; Drewnowski & Gomez-Carneros, 2000, American Journal of Clinical Nutrition 72: 1424-1435). Accordingly, these natural substances are economically important in such different fields as drugs, food additives, fragrances, pigments, and pesticides.

Secondary metabolites often accumulate in small quantities and sometimes only in specialized cells. Hence their extraction can be difficult and inefficient. In spite of the progress in organic chemical synthesis, a large number of these metabolites have such complex structures that they are virtually impossible to synthesize at economic levels. Moreover, the natural product is generally more acceptable to consumers than an artificially produced one. Consequently, industrial application of these substances and their functional analogues often relies on natural extraction from plants.

Secondary metabolites may generally be structurally qualified as low molecular weight organic compounds.

Industrial production of secondary metabolites or other natural and non natural low molecular weight organic compounds can be facilitated by a biotechnological approach. By transformation of genes involved in the biosynthesis of a desired natural product, plants or microbes can e.g. be manipulated to produce a compound not previously present in the plant or organism.

Glycosyltransferase may be defined as an enzyme which transfers residues of sugars (galactose, xylose, rhamnose, glucose, arabinose, glucuronic acid, etc) to acceptor molecules. Acceptor molecules may be other sugars, proteins, lipids and other organic substrates. The acceptor molecule may be termed an aglycon (aglucone if sugar is glucose). An aglycon may be defined as the non-carbohydrate part of a glycoside. A glycoside may be defined as an organic molecule with a glycosyl group (organic chemical group derived from a sugar or polysaccharide molecule) connected to it by way of e.g. an intervening oxygen, nitrogen or sulphur atom.

These glycosylated molecules take part in diverse metabolic pathways and processes. The transfer of a glycosyl moiety can alter the acceptor's bioactivity, solubility, stability, taste, scent and transport properties e.g. within a plant or microbial cell and throughout the plant.

The art describes a number of glycosyltransferases that can glycosylate compounds such as secondary metabolites from e.g. plants and fungi (Paquette, S. et al, Phytochemistry 62 (2003) 399-413).

WO01/07631, WO01/40491 and (Arend, J et al., Biotech. & Bioeng (2001) 78:126-131) describe that at least some of these glycosyltransferases are capable of glycosylating a number of different structurally related secondary metabolites and other structurally related low molecular weight organic compounds.

Accordingly, the skilled person has at his disposal a number of different glycosyltransferases capable of glycosylating numerous different secondary metabolites and other structurally related low molecular weight organic compounds.

Tattersall, D B et al, Science (2001) 293:1826-8 describes that the entire pathway for synthesis of the tyrosine-derived cyanogenic glucoside dhurrin [a seconday metabolite] has been transferred from the plant *Sorghum bicolor* to the plant *Arabidopsis thaliana*. The entire pathway for synthesis included two genes involved in the biosynthesis pathway (CYP79A1 and CYP71E1) and a glucosyltransferase (sbHMNGT) capable of glucosylating the last intermediate (p-hydroxymandelonitrile) to get the glucoside dhurrin (see FIG. 1 herein). It was demonstrated that the transgenic *Arabidopsis thaliana* plant was capable of producing 4 mg of dhurrin per gram of fresh weight.

Arend, J et al., Biotech. & Bioeng (2001) 78:126-131 and WO01/07631 describes cloning of a glucosyltransferase from the plant *Rauvolfia serpentina*. The cloned glucosyltransferase was inserted into *E. coli* bacteria. When the aglucones hydroquinone, vanillin and p-hydroxyacetophenone were added to the medium of cultivated cells of the engineered *E. coli*, the corresponding glucosides, arbutin, vanillin-D-glucoside and picein were synthesized. They also were released from the cells into the surrounding medium.

Moehs, C P et al, Plant Journal (1997) 11:227-236 describes that a cDNA encoding a solanidine glucosyltransferase (SGT) was isolated from potato. The cDNA was selected from a yeast expression library using a positive selection based on the higher toxicity of steroidal alkaloid aglycons relatively to their corresponding glycosylated forms. The activity of the cloned SGT was tested in an in vitro assay based on isolated recombinant produced SGT.

U.S. Pat. No. 6,372,461 describes a method for making the secondary metabolite vanillin by use of an *E. coli* cell where there has been introduced genes involving in the biosynthesis pathway starting from glucose and leading to vanillic acid. The recombinant *E. coli* can produce vanillic acid when cultured in a medium comprising glucose. The produced vanillic acid is recovered from the fermentation broth and reduced to vanillin with aryl-aldehyde dehydrogenase.

SUMMARY OF THE INVENTION

The problem to be solved by the present invention is to provide a new method of producing in particular low molecular weight organic compounds of interest, wherein the method provides the possibility of obtaining the compound in higher yields.

Among other things, the solution is based on that the present inventors have investigated and compared the following two cultivated microorganisms:

(i) a microorganism comprising a gene involved in the biosynthesis pathway leading to a low molecular weight aglycon compound; and (ii) the same microorganism but where there is also introduced a glycosyltransferase gene capable of glycosylating the produced aglycon to get the associated glycosylated form of the aglycon.

The inventors found that the microorganism with the glycosyltransferase during culture fermentation is capable of producing higher amounts of the glycosylated form of the aglycon as compared to the amounts of the corresponding aglycon produced by the microorganism without the glycosyltransferase. See working examples herein for an illustrative examples where (a) an *E. coli* cell of type (ii) above produces higher amounts of vanillin glucoside as compared to the amounts of the corresponding vanillin aglucone produced in a corresponding *E. coli* without the glycosyltransferase (*E. coli* cell of type (i) above);

(b) a yeast cell of type (ii) above produces higher amounts of vanillin glucoside as compared to the amounts of the corresponding vanillin aglucone produced in a corresponding yeast cell without the glycosyltransferase (yeast cell of type (i) above);

(c) a yeast cell of type (ii) above produces higher amounts of protocatechuic acid-β-D-glucoside (PAG) as compared to the amounts of the corresponding protocatechuic acid (PA) aglucone produced in a corresponding yeast cell without the glycosyltransferase (yeast cell of type (i) above);

(d) a yeast cell of type (ii) above produces higher amounts of dhurrin as compared to the amounts of the p-hydroxymandelonitrile (aglycone of dhurrin. See FIG. 1) produced in a corresponding yeast cell without the glycosyltransferase (yeast cell of type (i) above);

(e) a yeast cell of type (ii) above produces higher amounts of glucosylated compounds (such as e.g. p-glucosyloxy-phenylethanol, p-glucosyloxy-phenylacetonitrile, p-glucosyloxy-benzaldehyde or glucosyl p-hydroxybenzoate) derived from the Dhurrin biosynthesis pathway as compared to the amounts of corresponding aglycons produced in a corresponding yeast cell without the glycosyltransferase (yeast cell of type (i) above).

Accordingly, a microorganism cell of the type (ii) above may then be used to obtain the glycosylated form of the corresponding aglycon in high amounts. However, it may also be used in a process to make the aglycon in higher amounts simply by e.g. first making the glycosylated form of the aglycon, recovering it and deglycosylate it according to standard protocols (e.g. enzymatically by use of a β-glucosidase or by adequate chemical hydrolysis.)

Accordingly, a first aspect of the invention relates to a method of producing a low molecular weight organic compound comprising following steps:

a) fermenting a microorganism cell or a filamentous fungi cell, which comprises a gene encoding a product involved in the biosynthetic pathway leading to a low molecular weight organic aglycon compound and a heterologous glycosyltransferase gene encoding a glycosyltransferase capable of glycosylating the produced aglycon, in a suitable medium, wherein the cell produces the aglycon and the corresponding glycosylated form of the aglycon; and b) recovering the glycosylated form of the aglycon compound;

(i) wherein the low molecular weight organic aglycon compound has a molecular weight from 50 to 3000 g/mol, and (ii) wherein the glycosyltransferase is a glycosyltransferase capable of conjugating a sugar to the aglycon compound, wherein the sugar is a sugar selected from the group consisting of galactose, glucosamine, N-acetylglucosamine, xylose, glucuronic acid, rhamnose and glucose.

A second aspect of the invention relates to a microorganism cell or a filamentous fungi cell that comprises a gene encoding a product involved in the biosynthetic pathway leading to a low molecular weight organic aglycon compound and a heterologous glycosyltransferase gene encoding a glycosyltransferase capable of glycosylating the produced aglycon, wherein the cell, when fermented in a suitable medium, produces the aglycon and the corresponding glycosylated form of the aglycon, and wherein the glycosyltransferase is a glycosyltransferase capable of conjugating a sugar to the aglycon compound, wherein the sugar is a sugar selected from the group consisting of galactose, glucosamine, N-acetylglucosamine, xylose, glucuronic acid, rhamnose and glucose.

As said above, the basic principle behind the method described above may be used to produce an aglycon of interest in higher yields (overproduction of the aglycon of interest).

Accordingly, a third aspect of the invention relates to a method of producing a low molecular weight organic aglycon compound comprising following steps:

a) growing a cell, which comprises a gene encoding a product involved in the biosynthesis pathway leading to a low molecular weight organic aglycon compound and a glycosyltransferase gene encoding a glycosyltransferase capable of glycosylating the produced aglycon, under suitable conditions wherein the cell produces the aglycon and the associated glycosylated form of the aglycon;

b) deglycosylating the glycosylated form of the aglycon; and c) recovering the aglycon compound;

(i) wherein the low molecular weight organic aglycon compound has a molecular weight from 50 to 3000, and (ii) wherein the glycosyltransferase is a glycosyltransferase capable of conjugating a sugar to the aglycon compound.

An advantage of using a glycosyltransferase in a method as described herein may further be to use the different specificities of known glycosyltransferases. For instance, it is known that some glycosyltransferases are enantiomer specific (see e.g. Jones, P et al, J. of Biological Chemistry (1999), 274: 35483-35491 and WO03/023035). Consequently, if one for instance wants to make a specific enantiomer for e.g. an aglycon then one could choose to use such an enantiomer specific glycosyltransferase.

A fourth aspect of the invention relates to a method for selecting a cell with increased production of a glycosylated form of a low molecular weight organic aglycon compound comprising following steps:
- a) growing a cell, which comprises a gene encoding a product involved in the biosynthesis pathway leading to a low molecular weight organic aglycon compound and a glycosyltransferase gene encoding a glycosyltransferase capable of glycosylating the produced aglycon, under suitable conditions wherein the cell produces the aglycon and the corresponding glycosylated form of the aglycon;
- b) treating the cell in a way that changes the expression level of at least one gene involved in the biosynthesis pathway leading to a low molecular weight organic aglycon and/or the glycosyltransferase gene capable of glycosylating the produced aglycon in order to make a library of cells with different expression levels of the genes; and
- c) selecting a cell that produces a higher amount of the glycosylated form of the aglycon as compared to the cell of step a);
  - (i) wherein the low molecular weight organic aglycon compound has a molecular weight from 50 to 3000, and
  - (ii) wherein the glycosyltransferase is a glycosyltransferase capable of conjugating a sugar to the aglycon compound.

Example 8 herein describes how this method is used to make an *Arabidopsis thaliana* plant capable of producing increased mg of the glucoside dhurrin per gram of fresh weight. The starting cell of step a) is the *Arabidopsis thaliana* transgenic cell described in Tattersall, D B et al, Science (2001) 293:1826-8. As explained above the *Arabidopsis thaliana* transgenic cell comprises the entire pathway for synthesis of the cyanogenic glucoside dhurrin. It was demonstrated that the transgenic *Arabidopsis thaliana* plant was capable of producing 4 mg of dhurrin per gram of fresh weight. After performing the selecting method as described in example 8 an *Arabidopsis thaliana* transgenic cell is selected in step c) that produces more than 6 mg of dhurrin per gram of fresh weight.

Without being limited to theory, it is believed to be the first time that a transgenic plant has been provided that is capable of producing more than 4 mg per gram of fresh weight of a glycosylated form of a low molecular weight organic aglycon compound.

Accordingly, a fifth aspect of the invention relates to a transgenic plant capable of producing more than 5 mg per gram of fresh weight of a glycosylated form of a low molecular weight organic aglycon compound,
- (i) wherein the low molecular weight organic aglycon compound has a molecular weight from 50 to 3000.

DEFINITIONS

Prior to a discussion of the detailed embodiments of the invention is provided a definition of specific terms related to the main aspects of the invention.

The term "aglycon" denotes non-carbohydrate part of the corresponding glycosylated form of the aglycon. It may also be defined as an acceptor compound capable of being conjugated to a sugar. In a number of relevant examples, the aglycon is an alcohol with a hydroxy group suitable for being glycosylated. An example of this is p-hydroxymandelonitrile (see FIG. 1) which has a hydroxy group that can be conjugated (glycosylated) with glucose to get dhurrin. (dhurrin is here the corresponding glycosylated form of the aglycon p-hydroxymandelonitrile). In this example, wherein the sugar is glucose the aglycon may be termed aglucone. Further, when the sugar is glucose the term glucosylated may be used instead of glycosylated.

An aglycon may also be glycosylated at different group than a hydroxy group, in particular at other nucleophilic groups such as a carboxylic acid, SH—, nitrogen, amine, imine or C—C group.

The term "gene encoding a product involved in the biosynthesis pathway leading to a low molecular weight aglycon compound" should be understood according to the art as a gene encoding a product involved in the biosynthesis pathway leading to a low molecular weight aglycon compound. The gene encoded product is normally a polypeptide. However the product may also for instance be a RNA molecule affecting the expression of a gene. The encoded product of the gene may be directly involved in the biosynthesis pathway or indirectly via e.g. other precursors or intermediated. The important issue, independently of the precise mechanism behind it, is that the gene makes it possible for the cell to synthesize the aglycon compound of interest as described herein. The art describes numerous suitable examples of such genes. Just for illustration one example could be CYP71A1 from *Sorghum bicolor* that starting from p-hydroxyphenylacetonitrile is involved the biosynthesis pathway leading to a low molecular weight aglycon compound p-hydroxymandelonitrile (see FIG. 1 herein and Tattersall, D B et al, Science (2001) 293: 1826-8). Further examples are the genes involved in the biosynthesis pathway leading to a low molecular weight aglycon compound vanillin as described in working examples herein.

The term "glycoside" denotes a compound which on hydrolysis gives a sugar and a non-sugar (aglycon) residue, e.g. glucosides give glucose, galactosides give galactose.

The term "glycosyltransferase" denotes a glycosyltransferase capable of conjugating a sugar to an aglycon as described herein. The sugar may e.g. be D and L isomers of galactose, glucosamine, N-acetylglusamine, xylose, glucuronic acid, rhamnose, arabinose, mannose or glucose. Alternatively the sugar may be a carbohydrate derivative such as e.g. inositol, D-olivose, rhodinose and etc available as nucleotide diphosphates. Further the sugar may for instance be e.g. a monosaccharide, a disaccharide or a trisaccharide. In the case of oligo- and polysaccharides the sugars are linked one by one, by e.g. involving use of one or several glucosyltransferases. Further, a list of suitable sugars can be seen in US2003/0130205A1 paragraphs [0029] to [0036]. If the sugar is glucose the glycosyltransferase may be termed a glucosyltransferase.

The term "growing a cell" in relation to step a) of the third aspect should be understood broadly in the sense of growing a cell under suitable conditions (temperature, nutrients etc.) that allows growth of the cell. If the cell is e.g. a plant cell this means e.g. growth of the plant cell under conditions where e.g. a mature plant is obtained. If the cell is a microorganism this could e.g. be fermenting of the microorganism cell in a suitable medium where the microorganism is capable of growing.

The term "recovering" in relation to "recovering the glycosylated form of the aglycon compound" of step b) of the first aspect of the invention and "recovering the aglycon compound" of step c) of third aspect of the invention should be understood broadly in the sense that the compound is recovered from the cell or from e.g. the supernatant of the medium where the cell for instance is fermented in order to get the compound in a higher purity than before the recovery step. The recovery step may include more or less detailed purification steps. Preferably the compound is at some point after the recovery step present in a composition where the composition comprises at least 4% (w/w) of the compound, more preferably at least 10% (w/w) of the compound, even more preferably at least 20% (w/w) of the compound and most preferably at least 50% (w/w) of the compound. The skilled person is aware of suitable purification protocols (e.g. by using adequate purification columns) to obtain the desired purity.

Preferably after recovering there is recovered at least 10 mg compound, more preferably there is recovered at least 1 g compound, even more preferably there is recovered at least 10 g compound, and most preferably there is recovered at least 500 g compound. Preferably there is recovered from 10 mg to 100 kg compound.

Embodiment(s) of the present invention is described below, by way of example(s) only

DRAWINGS

FIG. 1: Shows the pathway for synthesis of the tyrosine-derived cyanogenic glucoside dhurrin (a seconday metabolite). The pathway for synthesis included two genes involved in the biosynthesis pathway (CYP79A1 and CYP71E1) and a glucosyltransferase (sbHMNGT) capable of glucosylating the last intermediate (p-hydroxymandelonitrile) to get the glucoside dhurrin.

DETAILED DESCRIPTION OF THE INVENTION

Cell

The cell suitable to growth as specified under step a) of the method of the third aspect of the invention may be any suitable cell such as any eukaryotic or prokaryotic cell. Preferably the cell is a cell selected from the group consisting of a plant cell, a filamentous fungal cell and a microorganism cell.

As explained above one of the primary advantages of use of the cell as described herein is that one can use it to get higher yields (get overproduction) of the glycosylated form of the aglycon or, after a suitable step of deglycosylating the glycosylated form of the aglycon, get higher yields (get overproduction) of the aglycon.

Accordingly a preferred cell is a cell wherein the cell with the glycosyltransferase during growing is capable of producing higher amounts of the glycosylated form of the aglycon as compared to the amounts of the corresponding aglycon produced by the cell without the glycosyltransferase.

When the cell is a microorganism cell this may e.g. be expressed as, wherein the microorganism cell with the glycosyltransferase during culture fermentation is capable of producing higher amounts of the glycosylated form of the aglycon as compared to the amounts of the corresponding aglycon produced by the same microorganism cell without the glycosyltransferase.

Preferably the cell (in particular a microorganism cell) should, when it comprises the glycosyltransferase, produce at least 1.1 times higher amounts of the glycosylated form of the aglycon as compared to the amounts of the corresponding aglycon produced by the same microorganism cell without the glycosyltransferase, more preferably at least 1.25 times higher amounts of the glycosylated form of the aglycon, even more preferably at least 1.5 times higher amounts of the glycosylated form of the aglycon and most preferably at least 2 times higher amounts of the glycosylated form of the aglycon.

A main advantage of the present invention relates to this overproduction of the glycosylated form of the aglycon and the term relating to higher production of the glycosylated form of the aglycon should therefore be understood in view of this and as generally understood by the skilled person. Consequently, the higher amounts of the glycosylated form of the aglycon may be accumulated within the cell where it can be recovered e.g. after lysis of the cell. Alternatively, the glycosylated form of the aglycon may e.g. be secreted from the cell and therefore accumulates in e.g. the culture media. The latter is particular relevant when the cell is a microorganism cell.

Plants which include a plant cell according to the invention are also provided as are seeds produced by said plants.

In a preferred embodiment of the invention said plant is selected from: corn (*Zea. mays*), canola (*Brassica napus, Brassica rapa* ssp.), alfalfa (*Medicago sativa*), rice (*Oryza sativa*), rye (*Secale cerale*), sorghum (*Sorghum bicolor, Sorghum vulgare*), sunflower (*helianthus annuas*), wheat (*Tritium aestivum* and other species), Triticale, Rye (*Secale*) soybean (*Glycine max*), tobacco (*Nicotiana tabacum*), potato (*Solanum tuberosum*), peanuts (*Arachis hypogaea*), cotton (*Gossypium hirsutum*), sweet potato (*Impomoea batatus*), cassaya (*Manihot esculenta*), coffee (*Cofea* spp.), coconut (*Cocos nucifera*), pineapple (*Anana comosus*), citrus (*Citrus* spp.) cocoa (*Theobroma cacao*), tea (*Camellia senensis*), banana (*Musa* spp.), avacado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Primus amygdalus*), apple (*Malus* spp), Pear (*Pyrus* spp), plum and cherry tree (*Prunus* spp), *Ribes* (currant etc.), *Vitis*, Jerusalem artichoke (*Helianthemum* spp), non-cereal grasses (Grass family), sugar and fodder beets (*Beta vulgaris*), chicory, oats, barley, vegetables, and ornamentals.

Preferably, plants of the present invention are crop plants (for example, cereals and pulses, maize, wheat, potatoes, tapioca, rice, sorghum, millet, cassaya, barley, pea, sugar beets, sugar cane, soybean, oilseed rape, sunflower and other root, tuber or seed crops. Other important plants maybe fruit trees, crop trees, forest trees or plants grown for their use as spices or pharmaceutical products (*Mentha* spp, clove, *Artemesia* spp, *Thymus* spp, *Lavendula* spp, *Allium* spp., *Hypericum, Catharanthus* spp, *Vinca* spp, *Papaver* spp., *Digitalis* spp, *Rawolfia* spp., *Vanilla* spp., *Petrusilium* spp., Eucalyptus, tea tree, *Picea* spp, *Pinus*. spp, *Abies* spp, *Juniperus* spp,. Horticultural plants to which the present invention may be applied may include lettuce, endive, and vegetable brassicas including cabbage, broccoli, and cauliflower, carrots, and carnations and geraniums.

The present invention may be applied in tobacco, cucurbits, carrot, strawberry, sunflower, tomato, pepper, Chrysanthemum.

Grain plants that provide seeds of interest include oil-seed plants and leguminous plants. Seeds of interest include grain seeds, such as corn, wheat, barley, nee, sorghum, rye, etc. Oil-seed plants include cotton soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava been, lentils, chickpea.

In a further preferred embodiment of the invention said plant is selected from the following group: maize, rice, wheat, sugar beet, sugar cane, tobacco, oil seed rape, potato and soybean.

The whole genome of *Arabidopsis thaliana* plant has been sequenced (Paquette, S. et al, Phytochemistry 62 (2003) 399-

413). Consequently, very detailed knowledge is available for this plant and it may therefore be a preferred plant cell to work with.

Accordingly, a very preferred plant cell is an *Arabidopsis* cell and in particular an *Arabidopsis thaliana* cell.

Filamentous fungi includes all filamentous forms of the subdivision Eumycota and Oomycota (as defined by Hawksworth et al., 1995, supra). The filamentous fungi are characterized by a vegetative mycelium composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred embodiment, the filamentous fungal cell is a cell of a species of, but not limited to, *Acremonium, Aspergillus, Fusarium, Humicola, Mucor, Myceliophthora, Neurospora, Penicillium, Thielavia, Tolypocladium,* and *Trichoderma* or a teleomorph or synonym thereof.

A preferred microorganism cell suitable to be used in a method as described herein is a microorganism cell selected from the group consisting of a yeast cell and prokaryotic cell.

A preferred yeast cell is a yeast cell selected from the group consisting of Ascomycetes, Basidiomycetes and fungi imperfecti. Preferably a yeast cell selected from the group consisting of Ascomycetes.

Preferred Ascomycetes yeast cell selected from the group consisting of *Ashbya, Botryoascus, Debaryomyces, Hansenula, Kluveromyces, Lipomyces, Saccharomyces* spp e.g. *Saccharomyces cerevisiae, Pichia* spp., *Schizosaccharomyces,* spp.

A preferred yeast cell is a yeast cell selected from the group consisting of *Saccharomyces* spp e.g. *Saccharomyces cerevisiae,* and *Pichia* spp.

In a method as described herein a very preferred cell is a prokaryotic cell. A preferred prokaryotic cell is selected from the group consisting of *Bacillus, Streptomyces, Corynebacterium, Pseudomonas*, lactic acid bacteria and in particular an *E. coli* cell.

A preferred *Bacillus* cell is *B. subtilis, B. amyloliquefaciens* or *B. licheniformis.*

A preferred *Streptomyces* cell is *S. setonii.*

A preferred *Corynebacterium* cell is *C. glutamicum.*

A preferred *Pseudomonas* cell is *P. putida* or *P. fluorescens*

A preferred cell is a cell without active at least some of the genes encoding a beta-glycosidase that deglycosylates the glycosylated form of the aglycon compound of interest to be produced as described herein. Further, it is preferred that the cell comprises a permease or other transport protein enabling the cell to release or secrete the glycoside to the medium or to an internal compartment than the one where it is glycosylated.

Transformation of suitable DNA containing vectors into the cells described above is routine work for the skilled person. Suitable vectors can be constructed, containing appropriate regulatory sequences, including promoter sequences, terminator fragments, polyadenylation sequences, enhancer sequences, marker genes and other sequences as appropriate. For further details see, for example Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for *Bacillus*". John Wiley and Sons, 1990).

In relation to examples of suitable plant cell vectors and suitable plant transformation techniques reference is made to WO02/103022. In relation to filamentous fungi cells reference is made to EP869167.

Preferably, the cell is a cell wherein the cell expresses a heterologous glycosyltransferase gene as described herein, in particular a microorganism cell or a filamentous fungi cell that expresses a heterologous glycosyltransferase gene as described herein.

In this connection, the term "heterologous glycosyltransferase gene" should be understood according to the art as a glycosyltransferase gene that has been introduced into a cell that, before the introduction, did not express the glycosyltransferase gene.

Alternatively, the glycosyltransferase gene may be an endogenous glycosyltransferase gene naturally produced by the cell.

Glycosyltransferase

As described above, the art describes a number of glycosyltransferases that can glycosylate a low molecular weight organic compound of interest such as secondary metabolites from e.g. plants and fungi. Based on DNA sequence homology of the sequenced genome of the plant *Arabidopsis thaliana* it is believed to contain around 100 different glycosyltransferases. These and numerous others have been analyzed in Paquette, S. et al, Phytochemistry 62 (2003) 399-413. FIG. 1 of this article is a so-called multiorganism tree providing names of numerous suitable glycosyltransferases.

WO01/07631, WO01/40491 and (Arend, J et al., Biotech. & Bioeng (2001) 78:126-131) describe that at least some of these glycosyltransferases are capable of glycosylating a number of different structurally related secondary metabolites and other structurally related low molecular weight organic compounds.

Further, numerous suitable sequences of glycosyltransferases may be found on the Carbohydrate-Active enZYmes (CAZY) database, which is availabe on the Internet at the CAZY website, copyrighted by AFMB-CNRS-Universités Aix-Marseille I & II.

In the CAZY database, there can de found suitable glycosyltransferase sequences from virtually all species including, animal, insects, plant, microorganisms.

Accordingly, the skilled person has at his disposal a number of different glycosyltransferases capable of glycosylating numerous different secondary metabolites and other low molecular weight organic compounds. This fact is described in further details below by way of some illustrative specific examples.

Although glucosyltransferases are generally thought to be relatively substrate specific it has been shown that other substrates can be processed at significant levels if they are presented to the enzyme. It has been shown that expression of the sorghum CYP79A1 in *Arabidopsis* resulted in the production of large amounts p-hydroxybenzylglucosinolate, which is not a naturally occuring glucosinolate (S-glucoside) of *Arabidopsis* (Bak et al, 2000, Plant Physiology 123: 1437-1448). The new glucosinolate is produced from p-hydroxyphenylacetaldoxime, which is formed from tyrosine by CYP79A1 and subsequently channeled into the pre-existing glucosinolate biosynthetic pathway and to the associated glucosyltransferases.

Moreover, a glucosyl transferase, arbutin synthase, isolated from the medicinal plant Rauvolfia serpentina was shown to have considerable activity to other substrates than the native hydroquinone (Arend et al, 2001, Biotechnology and Bioengineering 76: 126-131). When some of these substrates, like vanillin or p-hydroxyacetophenone, were fed to cultures of *E. coli* that had been engineered to express the plant glucosyl transferase the substances were taken up and converted to their corresponding glucosides, vanillin-β-D-glucoside and picein. These two products, both of which are of commercial interest, were subsequently released from the bacteria.

These examples show that glucosyl transferases can act on substrates that are normally not present in the metabolic pathway and that this can lead to the formation of novel glucosides of natural products.

As said above the skilled person has at his disposal a number of different glycosyltransferases capable of glycosylating numerous different secondary metabolites and other low molecular weight organic compounds. Further, he may by use of known routine methods easily identify further suitable glycosyltransferases capable of glycosylating specific low molecular weight organic compounds of interest. Below are given some examples of such suitable methods.

The numerous known DNA glycosyltransferase sequences may be used to make appropriate PCR primers to clone new glycosyltransferases. This could e.g. be done by a method comprising following steps:
(a) preparing a cDNA library from a cell (e.g. plant tissue cell) expressing glucosyltransferases,
(b) using relevant known DNA glycosyltransferase sequences to make appropriate PCR primers to amplify part of the glucosyltransferase cDNA from the cDNA library,
(c) using the DNA obtained in steps (b) as a probe to screen the DNA library prepared from cell expressing glucosyltransferases, and
(e) identifying and purifying vector DNA comprising an open reading frame encoding a glucosyltransferase of interest.

Alternatively, a suitable glucosyltransferase may be identified by use of a so-called expression cloning strategy. A suitable expression cloning strategy could be a method comprising following steps:
(a) preparing a cDNA library from a cell (e.g. plant tissue cell) expressing glucosyltransferases;
(b) introducing the cDNA library into expression cells by use of an expressing vector that gives expression (transcription and translation) of the cDNA in a growing expression cell of interest;
(c) growing the cell in a medium comprising a toxic amount of a low molecular weight organic aglycon compounds of interest (i.e. only specific individual cells comprising an expressed glucosyltransferase capable of glycosylating the aglycon of interest will be able to grow);
(d) isolating one or more of the growing cells and identify one that expresses the glucosyltransferase of interest.

As described in Moehs, C P et al, Plant Journal (1997) 11:227-236 this expression cloning strategy may be done by use of a yeast cell. The teaching of the present invention demonstrates that the glycosylated form of the aglycon is less toxic to bacteria as compared to the corresponding aglycon as such. Consequently, this expression cloning strategy may be done by use of bacterial cells such as *E. coli*.

Accordingly, a separate aspect of the invention relates to expression cloning method for obtaining a glucosyltransferase of interest comprising following steps:
(a) preparing a cDNA library from a cell (e.g. plant tissue cell) expressing glucosyltransferases;
(b) introducing the cDNA library into bacterial expression cells by use of an expression vector that gives expression (transcription and translation) of the cDNA in a growing expression cell of interest;
(c) growing the cell in a medium comprising a toxic amount of a low molecular weight organic aglycon compounds of interest (i.e. only specific individual cells comprising an expressed glucosyltransferase capable of glycosylating the aglycon of interest will be able to grow);
(d) isolating one or more of the growing cells and identify one that expresses the glucosyltransferase of interest.

Preferably, the bacterial expression cells of step (b) are *E. coli* cells.

An advantage of an expression cloning strategy as described above it that one directly gets a glucosyltransferase capable of glycosylating the aglycon of interest.

Preferably, the glycosyltransferase is a capable of conjugating a sugar to the aglycon compound, wherein the sugar is a sugar selected from the group consisting of galactose, glucosamine, N-acetylglucosamine, xylose, glucuronic acid, rhamnose, arabinose, mannose and glucose.

In a further preferred embodiment, the glycosyltransferase is a NDG-glycosyltransferase. Such glycosyltransferases have been identified in plants, animals, fungi, bacteria and viruses. These glycosyltransferases are characterized by utilization of NDP-activated sugar moeties as the donor molecule and contain a conserved UGT-defining sequence motif near the C-terminus.

In a more preferred embodiment, the glycosyltransferase is a UDPG-glycosyltransferase (UGT). UGTs have been identified in plants, animals, fungi, bacteria and viruses. These glycosyltransferases are characterized by utilization of UDP-activated sugar moeties as the donor molecule and contain a conserved UGT-defining sequence motif near the C-terminus. See (Paquette, S. et al, Phytochemistry 62 (2003) 399-413) for further details in relation to the definition of this UDPG-glycosyltransferase family.

Preferably, the glycosyltransferase is a glycosyltransferase that conjugates a monosaccharide or a disaccharide sugar to an aglycon as described herein. Most preferably glycosyltransferase is a glycosyltransferase that conjugates a monosaccharide sugar to an aglycon as described herein.

In a preferred embodiment, the glycosyltransferase is a glucosyltransferase.

Below are described examples of some suitable glycosyltransferases.

WO01/40491 describes cloning of a glycosyltransferase from the plant *Sorghum bicolor* named sbHMNGT. This and the related homologous glycosyltransferases as described in WO01/40491 are capable of glycosylating at least following low molecular weight organic aglycon compounds (see Table 3 of WO01/40491):

Cyanohydrins
1) mandelonitrile
p-hydroxymandelonitrile
3) acetone cyanohydrin
benzyl derivatives
4) hydroquinone
5) benzyl alcohol
6) p-hydroxybenzyl alcohol
7) benzoic acid
8) p-hydroxybenzoic acid
9) p-hydroxybenzaldehyde
10) gentisic acid
11) caffeic acid
12) 2-hydroxy cinnamic acid
13) resveratrol (stilbene)
14) salicylic acid
15) p-hydroxymandelic acid
16) vanillic acid
17) vanillin 18) 2-hydroxy methoxybenzylalcohol
flavonoids
19) quercetin (flavonol)
20) cyanidin (anthocyanidin)
21) biochanin A (isoflavone)
22) naringenin (flavanone)
23) apigenin (flavone)
hexanol derivatives
24) 1-hexanol
25) trans hexen-1-ol
26) cis hexen-1-ol
27) 3-methyl hexen-1-ol
28) 3-methyl hexen-1-ol
29) indole acetic acid (plant hormone)
30) geraniol (monoterpenoid)
31) tomatidine (alkaloid)
32) nerol
33) p-citronellol Arend, J et al., Biotech. & Bioeng (2001) 78:126-131 describes cloning of a glycosyltransferase from the plant *Rauvolfia serpentina*. It is capable of glycosylating at least following low molecular weight organic phenolic aglycon compounds (see table 1):

Hydroquinone, Vanillin, Saligerin, Resorcinol, Thymol, Phenol, Methylvanillin, p-Hydroxyacetophenone, Vanillic acid, p-Methoxyphenol, 3,4-Dimethoxyphenol, Coniferyl alcohol, o-Coumaric Acid, p-Coumaric Adic.

WO01/59140 describes a glycosyltransferase from the plant *Arabidopsis thaliana*. It is capable of glycosylating at least following low molecular weight organic aglycon compounds: caffeic acid, luteolin, quercitin-, catechinl-, syadinin.

WO02/103022 describes a glycosyltransferase from the plant *Arabidopsis thaliana*. It is capable of glycosylating at least following low molecular weight organic aglycon compounds:

Benzoate substrates, in particular p-hydroxybenzoic acid.

WO03/02035: describes a glycosyltransferase from the plant *Arabidopsis thaliana*. It is capable of glycosylating at least following low molecular weight organic aglycon phytohormone compound: Abscisic acid.

Below are described suitable assays to measure the activity of a glycosyltransferase of interest. The assays are described for a glucosyltransferase. However when sugar is not glucose, one just has to use the adequate sugar (e.g. galactose) in stead of the glucose.

The ability of a glucosyltransferase to conjugate an aglycon of interest to glucose can for example be determined in an assay comprising the following steps.

a) Incubation of a reaction mixture comprising $^{14}C$_UDP-glucose, aglycon and UDPglucose:aglycon-glucosyltransferase at 30° C. between 2 minutes and 2 hours
b) terminating the reaction, and
c) chemical identification and quantification of the glucoside produced.

Typically the reaction mixture has a volume of 5 to 2000 µl, but preferably 20 µl and includes 10-200 mM Tris HCl (pH 7.9); 1-5 µM $^{14}C$-UDP-glucose (about 11.0 GBq mmol-1); 0-300 µM UDP-glucose; 0-20 mM aglycone; 25 mM γ-gluconolactone; 0-2 µg/µl BSA and 0-10 ng/µl UDP-glucose: aglycon-glucosyltransferase. β-glucosidase inhibitors other than γ-gluconolactone and protein stabilizers other than BSA may be included as appropriate. One possibility to terminate the reaction is to acidify the reaction mixture for example by adding ⅒ volume of 10% acetic acid.

Chemical identification and quantification of the glucoside formed in the reaction mixture may be achieved using a variety of methodologies including NMR spectroscopy, TLC analysis, HPLC analyses or GLC analysis in proper combinations with mass spectrometric analysis of the glucoside.

Reaction mixtures for analysis by NMR spectroscopy usually have a total volume of 0.5-1 ml, are incubated for 2 hours and include 0-10 mM aglycon, e.g. 2 mM p-hydroxymandelonitrile or 6.5 mM geraniol, 3 mM UDP-glucose, 2.5 µg gluceryltransferease, and 0.5 mg BSA. Glucosides are extracted for example with ethyl acetate and lyophillized prior to NMR analysis.

For TLC analysis the reaction mixtures are applied to Silica Gel 60 F254 plates (Merck), dried and eluted in a solvent such as ethyl acetate:acetone:dichloromethane:methanol $H_2O$ (40: 30:12:10:8, v/v). Plates are dried for one hour at room temperature and exposed to storage phosphor imaging plates prior to scanning on a PhosphorImager. Based on the specific radioactivity of the radiolabelled UIDP-glucose, the amount of glucoside formed is quantified. The radioactivity may also be determined by liquid scintillation counting (LSC analysis). In some cases, where the glucoside formed is derived from a very hydrophobic aglycon, e.g. mandelonitrile, the glucoside can be extracted into an ethyl acetate phase and thereby be separated from unincorporated $^{14}C$-UDP-glucose. 2 ml of scintillation cocktail are added to 250 µl of each ethyl acetate extract and analyzed using a liquid scintillation counter. During column fractionation, those fractions containing gluceryltransferase activity can be identified using the aglycon substrate of interest and ethyl acetate extraction of the glucoside formed.

A glycosyltransferase gene as described herein may be introduced into a cell in order to make a cell wherein the cell expresses a heterologous glycosyltransferase gene as described herein, in particular a microorganism cell or a filamentous fungi cell that expresses a heterologous glycosyltransferase gene as described herein.

Alternatively, the glycosyltransferase gene may be an endogenous glycosyltransferase gene naturally produced by the cell.

In addition genes giving raise to increased expression of the glycosyltransferase or increased yield of the glycoside may be introduced, such genes may encode regulatory proteins, protease inhibitors, repressors of protease gene, genes increasing the level or precursors, especially the relevant NDP-sugars, genes involved in NDP-metabolism, permeases and other transporters, genes reducing the metabolism of the aglycone etc.

A Gene Involved in the Biosynthesis Pathway

As said above, the term a "gene encoding a product involved in the biosynthesis pathway leading to a low molecular weight aglycon compound" should be understood according to the art as a gene encoding a product involved in the biosynthesis pathway leading to a low molecular weight aglycon compound.

The art describes numerous suitable examples of such genes and the numbers are exponentially increasing since a number of whole genomes of different plant and microorganisms are continuously published.

Reference may for example be made to the textbook "Biochemistry & Molecular Biology of Plants", edited by Bob B. Buchanan et al, ISBN 0-943088-37-2. Chapter 24: "Natural Product (Secondary Metabolites)" describes examples of a number of different suitable genes involved in the biosynthesis pathway leading to a low molecular weight aglycon compound.

Just for illustration one example could be CYP71E1 from *Sorghum bicolor* that starting from p-hydroxyphenylacetonitrile is involved the biosynthesis pathway leading to a low molecular weight aglycon compound p-hydroxymandelonitrile (see FIG. 1 and Tattersall, D B et al, Science (2001) 293:1826-8).

Further examples are the genes involved in the biosynthesis pathway leading to a low molecular weight aglycon compound vanillin as described in working examples herein. Even further examples are given in Szczebara et al., Nature Biotechnology (2003), 21:143-149. This article describes a recombinant yeast cell capable of producing hydrocortisone from a simple carbon source. The yeast cell comprised eight recombinantly introduced genes involved in the biosynthesis pathway.

As said above the skilled person has at his disposal a number of different biosynthesis pathway genes. Further, he may by use of known routine methods easily identify further suitable biosynthesis pathway genes. For instance, the numerous biosynthesis pathway gene sequences may be used to make appropriate PCR primers to clone new suitable biosynthesis pathway genes. This could e.g. be done by a method comprising following steps:

(a) preparing a cDNA library from a cell (e.g. plant tissue cell) expressing biosynthesis pathway genes of interest,
(b) using relevant known biosynthesis pathway gene sequences to make appropriate PCR primers at to amplify part of the biosynthesis pathway gene encoding cDNA from the cDNA library,
(c) using the DNA obtained in steps (b) as a probe to screen the DNA library prepared from cell expressing the biosynthesis pathway genes of interest, and
(e) identifying and purifying vector DNA comprising an open reading frame encoding a biosynthesis pathway gene of interest.

As explained above a cell used in a method as described herein comprises a gene encoding a product involved in the biosynthesis pathway. The cell may comprise more than one gene encoding a product involved in the biosynthesis pathway.

A suitable example is the transgenic *Arabidopsis thaliana* cell described in Tattersall, D B et al, Science (2001) 293: 1826-8. It comprises the two biosynthesis pathway genes CYP79A1 and CYP71E1 and can therefore make aglycon compound p-hydroxymandelonitrile from tyrosine (see FIG. 1 herein).

A further example is the *E. coli* cell described in working examples herein that comprises sufficient biosynthesis pathway genes to make the aglycon vanillin from glucose.

A gene encoding a product involved in the biosynthesis pathway as described herein may be introduced into a cell in order to make a cell wherein the cell expresses a heterologous gene encoding a product involved in the biosynthesis pathway as described herein, in particular a microorganism cell or a filamentous fungi cell that expresses a heterologous gene encoding a product involved in the biosynthesis pathway as described herein.

Alternatively, the gene encoding a product involved in the biosynthesis pathway may be an endogenous gene naturally produced by the cell.

Low Molecular Weight Organic Aglycon Compound

As said above, the low molecular weight organic aglycon compound, as described herein, has a molecular weight from 50 to 3000. Preferably, the low molecular weight organic aglycon compound has a molecular weight from 50 to 2000, more preferably a molecular weight from 50 to 1000, and even more preferably a molecular weight from 50 to 750. The molecular weight is the mass of one molecule in atomic mass units.

Further, the low molecular weight organic aglycon compound is preferably a compound selected from the group consisting of more or less saturated Alkyl-, Cycloalkyl-, Cycloalkylalkyl-, Arallyl- and Aryl, with 1 to 50 C-atoms and 0 to 20 heteroatoms and optionally substituted, in particular with Hydroxy-, Amino-, Sulfide-, Carboxy-, or Nitro groups, at the 1 to 56 C-atoms and/or 0 to 20 Heteroatoms; more preferably a compound selected from the group consisting of more or less saturated Alkyl-, Cycloalkyl-, Cycloalkylalkyl-, Arallyl- and Aryl, with 1 to 32 C-atoms and 0 to 10 heteroatoms and optionally substituted, in particular with Hydroxy-, Amino-, Sulfide-, Carboxy-, or Nitro groups, at the 1 to 32 C-atoms and/or 0 to 10 Heteroatoms.

In a preferred embodiment, the low molecular weight organic aglycon compound is an alcohol, in particular an aromatic alcohol. An alcohol should herein be understood in relation to the technical objective of glycosylating the aglycon. Accordingly an aglycon defined as an alcohol is herein a compound that contains a hydroxyl- (—OH) functional group that can be glycosylated by use of a glycosyltransferase as described herein. A non limiting example of a preferred aglycon compound which is an aromatic alcohol is vanillin or p-hydroxymandelonitrile.

Alcohols also include e.g. some ketones, aldehydes and other compounds being in equilibrium with an alcohol, e.g. enols, furanosider, pyranosider, lactames and lactones etc.

In line of above, a preferred organic aglycon compound is an organic aglycon compound that comprises a compound that contains Hydroxy-, Amino-, Imino-, Thiol- -Sulfite, Sulfate, Phosphate or Phosphonate or Carboxy functional group that can be glycosylated by use of a glycosyltransferase as described herein. It may also be corresponding boron and selenium groups and compounds containing group being in equilibrium with the mentioned groups. Aglycons that comprises a hydroxyl-group is discussed immediately above.

In a preferred embodiment the organic aglycon compound is an organic aglycon compound that comprises a compound that contains a carboxy functional group that can be glycosylated by use of a glycosyltransferase as described herein to form an ester glycoside. A non limiting example of such aglycon compounds is vanillic acid or p-hydroxybenzoic acid.

In a preferred embodiment the low molecular weight organic aglycon compound is a pharmaceutical compound or a chemical intermediate of a pharmaceutical compound. A suitable pharmaceutical compound may be pharmaceutical compound produced naturally in an animal, a plant, a filamentous fungi or a microorganism.

A preferred pharmaceutical compound is a pharmaceutical compound selected from the list consisting of budesonide, raloxifine, tamoxifine, dopamine, steroids.

Further a description of suitable preferred pharmaceutical compounds can be found in US2003/0130205A1 and US2003/0119761A1.

In a preferred embodiment the low molecular weight organic aglycon compound is an aglycon compound selected from the list consisting of vitamin, amino acids, fatty acids, oligopeptide, oligosaccharide, oligonucleotide, PNA, LNA, and functional equivalents thereof. For this group of aglycon compounds the size of the compounds may have a bigger molecular weight than 3000.

Plants may be seen as the organic chemists per excellence in nature. More than 200.000 different natural products are known from plants. These enable plants to deter herbivores and pests, attract pollinators, communicate with other plants and constantly adapt to climatic changes. As explained before the majority of these compounds may be termed secondary metabolites.

The term "secondary metabolite" relates to that plants and microbes synthesize a large number of natural substances, in particular secondary metabolites, with diverse and generally unclear function. In contrast to the primary metabolites (eg amino acids, sugars, fatty acids), which are involved in fundamental functions like metabolism, growth, maintenance and survival, secondary metabolites are not required for fundamental functions. The term secondary metabolite should herein be understood in view of such, according to the art, standard description of the term.

In a preferred embodiment the low molecular weight organic aglycon compound is a secondary metabolite compound, preferably a plant secondary metabolite compound.

Examples of preferred secondary metabolite compound classes are:
Terpenoids
Alkaloids
Phenylpropanoids
Phenyl derivatives
Hexanol derivatives
Flavonoids
Coumarins, stilbenes
Cyanohydrins
Glucosinolates
Sterols
Saponin aglycones
Steroids
Hormones
Antibiotics
and Herbicides.

Of the list above, the more preferred secondary metabolite compound classes are:
Terpenoids
Alkaloids
Phenylpropanoids
Phenyl derivatives
Hexanol derivatives
Flavonoids
Coumarins, stilbenes
Cyanohydrins
and Glucosinolates.

Examples of preferred individual low molecular weight organic aglycon compounds is a compound selected from the list consisting of:

mandelonitrile, p-hydroxymandelonitrile, acetone cyanohydrin, hydroquinone, benzyl alcohol, p-hydroxybenzyl alcohol, benzoic acid, p-hydroxybenzoic acid, p-hydroxybenzaldehyde, gentisic acid, caffeic acid, 2-hydroxy cinnamic acid, resveratrol (stilbene), salicylic acid, p-hydroxymandelic acid, vanillic acid, vanillin, 2-hydroxy methoxybenzylalcohol, quercetin, cyanidin (anthocyanidin), biochanin A (isoflavone), naringenin (flavanone), apigenin (flavone), 1-hexanol, trans hexen-1-ol, cis hexen-1-ol, 3-methyl hexen-1-ol, 3-methyl hexen-1-ol, indole acetic acid (plant hormone), geraniol (monoterpenoid), tomatidine (alkaloid), nerol, p-citronellol, saligerin, resorcinol, thymol, phenol, methylvanillin, p-hydroxyacetophenone, p-methoxyphenol, 3,4-dimethoxyphenol, coniferyl alcohol, o-coumaric acid, p-coumaric adic, caffeic acid, luteolin, quercitin-, catechinl-, cyadinin, p-hydroxybenzoic acid, abscisic acid (phytohormone), 2,4,5-trichlorophenol (TCP), pentachlorophenol, 4-nitrophenol, 3,5-dibromo-4-hydrobenzoic acid, tetracycline, protocatechuic acid, 2-phenylethanol and 2,2-bis-(4-chlorophenyl)-acetic acid.

Growing a Cell

In a method as described herein, the cell should be grown under conditions where it produces the aglycon and the corresponding glycosylated form of the aglycon. An important point in relation to the growth of the cell is that adequate intermediate compounds must be available to the cell. This means for example that if the cell is e.g. an *E. coli* cell comprising adequate genes involved in the biosynthesis pathway leading e.g. to the aglycon compound vanillin from e.g. glucose, then the *E. coli* cell should be fermented under conditions where glucose is available to the cell.

If the cell is e.g. a plant cell comprising adequate genes involved in the biosynthesis pathway leading to the aglycon compound from e.g. tyrosine then the plant cell should be grown under conditions where suitable amount of tyrosine is present to the growing plant.

The skilled person knows how to grow a specific cell of interest to ensure this.

A Method of Producing a Low Molecular Weight Organic Aglycon Compound

As described above the third aspect of the invention relates to a method of producing a low molecular weight organic aglycon compound comprising following steps:
a) growing a cell, which comprises a gene encoding a product involved in the biosynthesis pathway leading to a low molecular weight organic aglycon compound and a glycosyltransferase gene encoding a glycosyltransferase capable of glycosylating the produced aglycon, under suitable conditions wherein the cell produces the aglycon and the associated glycosylated form of the aglycon;
b) deglycosylating the glycosylated form of the aglycon; and
c) recovering the aglycon compound;
(i) wherein the low molecular weight organic aglycon compound has a molecular weight from 50 to 3000, and
(ii) wherein the glycosyltransferase is a glycosyltransferase capable of conjugating a sugar to the aglycon compound.

All embodiments above are also embodiments of this third aspect. An essential step of this method is the deglycosylating step b). This step is further described below, where some non-limiting examples are included to illustrate a number of technical advantages in relation to this deglycosylating step.

Though glucosides are often desirable natural products and attempts to use transgenic glucosyl transferases to produce them have been taken (e.g. Arend et al, 2001, Biotechnology and Bioengineering 76: 126-131) the corresponding aglucone can be more commercially interesting. One example is vanillin, a natural flavour of significant commercial interest. Vanillin is a phenolic compound that accumulates in the fruits of the orchid *Vanilla* sp. in a glycosylated form, gluco-vanillin. In order to obtain the desired natural flavour, glucovanillin must be deglucosylated. This is achieved by fermentation (curing) of the fruits, so-called vanilla beans, whereby endogenous beta-glucosidases are activated.

In the step b) of the method of the third aspect of the invention, the glycosylated intermediate of the desired natural product is subjected to a deglycosylating step. This may be done by chemical hydrolysis according to known methods in the art or enzymatically by e.g. use an enzyme with beta-glycosidase activity. Numerous suitable beta-glycosidases are known to the skilled person. This can e.g. be achieved first by recovering glycosylated form of the aglycon for instance by extracting the glucosylated intermediate in a suitable solvent, e.g. methanol, or by collecting it after excretion from the producing organism or plant. Secondly, the glucosylated intermediate is purified and exposed to a beta-glucosidase in vitro or to an adequate chemical hydrolysis.

Alternatively, the stabilized glucosylated intermediate can be let alone in the plant and be allowed to accumulate in cellular compartments or tissues where it is protected from endogenous beta-glucosidase activity. In such a protected spatial environment the glucosylated intermediate is no longer exposed to enzymatic activity that could further metabolize its deglucosylated equivalent. The glycoside may also be modified .e.g. by acetylation or other modifications and in that way be protected from glycosidases. It could, however, also be protected in time, if the desired natural product was kept in its glucosylated form until developmental changes in the plant had led to a significant decrease in the activity of the enzymes that could otherwise metabolize its deglucosylated form.

It is preferred for the present invention that glycosylation of the desired aglycon is uncoupled from its subsequent deglycosylation, since the aglycon would otherwise be subject to further metabolic processing. As indicated above, this uncoupling can be either in time or space. Preferably it is in space.

In the final step c) of the method of the third aspect of invention, the desired aglycon is recovered.

The present method will address at least three problems related to biotechnological production of organic molecules. First, it will allow for increased production of organic molecules that are stable and constitute the final product of the respective biosynthetic pathway of the production organism. Second, it will allow for increased yield of organic molecules that are not the end product of the respective biosynthetic pathway and are consequently further metabolized by the production organism. Third, it will allow for increased production of organic molecules that are toxic to the production organism.

Regarding toxicity is show in examples 1 and 2 that the presence of a heterologous UDPG-glucosyltransferase in a microorganism can increase its tolerance to vanillin through glucosylation. This principle is evidently not limited to vanillin but can be applied to any toxic substance that can be converted into a less toxic glucoside by the heterologous UDPG-glucosyltransferase, including e.g. taxol.

This approach can be helpful in increasing tolerance to a desired organic molecule, which is the end product of its biosynthetic pathway and is therefore accumulated in the production organism to concentrations that might be limiting production. However, the approach might also address detoxification of substances that are structurally or biosynthetically unrelated to the desired molecule. Such substances could be byproducts of the desired biosynthetic pathway or contaminants in the growth medium.

In the industrial fermentation of ethanol from lignocellulose, vanillin has been reported to be one of the strongest inhibitors among the hydrolysis byproducts (Delgenes et al, 1996, Enzyme Microb Technol, 19: 220) and it acts as a strong growth inhibitor at concentrations of 5 g/l in the medium (Pfeifer et al, 1984, Biotechnol Lett 6: 541). Accordingly, fermentation of lignocellulose using microorganisms expressing a heterologous UDPG-glucosyltransferase might not only increase the yield of ethanol but could potentially also lead to a means for parallel production of commercially valuable vanillin after recovery and deglucosylation of non-toxic vanillin glucoside.

The method as described herein are of direct importance to biotechnological production of several organic molecules, since it can increase yield of organic molecules that are stable and constitute the final product of the respective biosynthetic pathway of the production organism. The feasibility of this approach is shown in examples 3 and 4 using production of vanillin in a microbial system as an example. However, it is obvious for those skilled in the art that this principle is not limited to production of vanillin from ferulic acid, but can be applied in virtually any biosynthetic pathway where the desired organic molecule is the end product and opposes at least some inhibition to production.

When the desired organic molecule is the end product of its biosynthetic pathway it will itself in many cases be a limiting factor in the rate of production. This is due to product inhibition of enzymes in the biosynthetic pathway and thus leads to reduced production rate. Instead of achieving high levels of the desired end product, an intermediate product might build up and either accumulate or be directed into other metabolic pathways and consequently become lost for the desired biosynthetic pathway.

The method will overcome this product inhibition by adding an additional step to the biosynthetic pathway, so the inhibiting product is removed and thereby is no longer able to inhibit the enzyme. When biosynthesis is no longer suppressed by product inhibition the turnover of the initial substrates and their conversion into first the desired product and subsequently into its glucosylated derivative will substantially increase. According to the method, the glucosylated derivative is then extracted and converted back into the desired aglucone by e.g. beta-glucosidase activity.

The desired organic molecule might, however, not always be the end product of its biosynthetic pathway in the production organism. In such cases, it is further metabolized and might eventually be lost for commercial recovery. In examples 5 and 6 is demonstrated how the method can be applied to rescue such intermediates. In the examples, an aldehyde oxime is rescued by glucosylation of a heterologous UDPG-glucosyltransferase, but it is evident for those skilled in the art that the principle is general and can be used for any intermediate product of desire that can be glucosylated. The examples address a molecule of desire, the oxime aldehyde, which is not naturally produced in the production organism, but in other examples the organic molecule of desire might as well be a substance that is produced naturally.

The sorghum cytochrome P450 enzyme complex CYP79 catalyses the conversion of the amino acid tyrosine into an aldehyde oxime, p-hydroxyphenylacetaldoxime (Bak et al, 2000, Plant Physiol 123: 1437). Attempts to transfer the sorghum CYP79 gene to other plants or microorganisms leads to very low production of the oxime, since it is toxic and is being further metabolised to at least two presently unidentified substances, X and Y, that might be nitrile and alcohol derivates (Halkier et al, 1995, Arch Biochem Biophys 322: 369; Bak et al, 2000, Plant Physiol 123: 1437). In plants, e.g. tobacco and *Arabidopsis*, the oxime is also glucosylated into p-hydroxyphenyl-(acetaldoxime glucoside) by an oxime specific UDPG-glucosyl transferase.

It is a general principle of the method that a glucosylated form of the desired organic molecule becomes the final product produced in the production organism. In addition to the advantages this principle can have in yield, it might also posses some benefits during purification or extraction of the desired organic molecule. This is demonstrated in example 7, where it is exploited that the solubility of the desired molecule changes after glucosylation.

This principle can be useful if the desired molecule is difficult to separate from other substances present in the production organism or the growth medium. The glucosylated form could e.g. be exported to another compartment than the contaminating molecule, thereby facilitating purification. Alternatively, it could be excreted to the growth medium, whereas the contaminating molecule is left alone within the organism. Moreover, the purification process could utilize that the glucosylated form of the desired molecule has novel chemical properties, including not only solubility but also chromatographic properties etc.

Method to Selecting Transgenic Organisms with Increased Biosynthesis Flow

In example 6, is shown an example of how the method of the third aspect of the invention can be utilized to establish commercial production of p-hydroxyphenylacetaldoxime in microorganisms. This is achieved by transferring both the sorghum CYP79 gene and the oxime specific UDPG-glucosyltransferase (see FIG. 1) into the microorganism. This results in the production of p-hydroxyphenyl-(acetaldoxime glucoside), which is stable and non-toxic. Moreover, this glucoside can be extracted and converted into the desired p-hydroxyphenylacetaldoxime by e.g. in vitro beta-glucosidase activity.

Using this approach, the method not only makes the production of the desired molecule, the oxime, possible. It also allows for the selection of transgenic microorganisms with high expression levels of the sorghum CYP79 in a very active form, since the toxic product of the enzyme is readily detoxified by glucosylation. If the oxime specific UDPG-glucosyl transferase was not present, natural selection would favor microorganisms harboring the CYP79 gene in a low expressing state and in a mutated form with less activity.

The example discussed above, illustrates how the method can be utilized to obtain, through selection, more efficient production organisms. This principle is not restricted to the example above, but will obviously apply for many other biosynthetic pathways and production organisms.

Accordingly, as said above a fourth aspect of the invention relates to a method for selecting a cell with increased production of a glycosylated form of a low molecular weight organic aglycon compound comprising following steps:
 a) growing a cell, which comprises a gene encoding a product involved in the biosynthesis pathway leading to a low molecular weight organic aglycon compound and a glycosyltransferase gene encoding a glycosyltransferase capable of glycosylating the produced aglycon, under suitable conditions wherein the cell produces the aglycon and the corresponding glycosylated form of the aglycon;
 b) treating the cell in a way that changes the expression level of at least one gene involved in the biosynthesis pathway leading to a low molecular weight organic aglycon and/or the glycosyltransferase gene capable of glycosylating the produced aglycon in order to make a library of cells with different expression levels of the genes; and
 c) selecting a cell that produces a higher amount of the glycosylated form of the aglycon as compared to the cell of step a);
  (i) wherein the low molecular weight organic aglycon compound has a molecular weight from 50 to 3000, and
  (ii) wherein the glycosyltransferase is a glycosyltransferase capable of conjugating a sugar to the aglycon compound.

The term "library of cells" may herein also be termed "population of cells". The library of cells may comprise as little as two different cells.

The term "different expression levels of the genes" may be a library comprising individual cells with both increased or decreased expression levels of the genes. Preferably, the library mainly comprises individual cells with increased expression levels of the genes.

Wherein the cell is within a plant the library will comprise a library of different plants. Preferably the library comprises $10^2$ plants, more preferably $10^3$ plants, even more preferably $10^5$ plants, even more preferably $10^6$ plants.

When the cell is a microorganism the library may normally easily be made relatively bigger. Consequently, when the cell is a microorganism the library comprises $10^5$ cells, more preferably $10^7$ cells, even more preferably $10^8$ cells, even more preferably $10^9$ cells.

The selected cell of this method may be a preferred cell to use in a method of producing a low molecular weight organic compound of the first aspect of the invention or a method of producing a low molecular weight organic aglycon compound of the third aspect of the inventions or in relation to the different embodiments of these methods to make a low molecular weight organic compound.

Accordingly, an embodiment of the invention relates to a method where there is first selected a cell as described in the fourth aspect above and thereafter this cell is used in a method of producing a low molecular weight organic compound of the first aspect of the invention or a method of producing a low molecular weight organic aglycon compound of the third aspect of the inventions or in relation to the different embodiments of these methods to make a low molecular weight organic compound.

The treating of the cell step b) above may be done by numerous different strategies known to the skilled person. Examples are mutagenesis such as UV treatment, adequate chemical treatment to make DNA mutations, random mutagenesis of e.g. specific promoters of the relevant genes, shuffling of cells to make a library of shuffled cells and etc.

The selected cell of step c) should preferably produce 1.25 times higher amounts of the glycosylated form of the aglycon as compared to the cell of step a), more preferably the selected cell of step c) should preferably produce 1.5 times higher amounts of the glycosylated form of the aglycon as compared to the cell of step a), even more preferably the selected cell of step c) should preferably produce 2 times higher amounts of the glycosylated form of the aglycon as compared to the cell of step a), and most preferably the selected cell of step c) should preferably produce 3 times higher amounts of the glycosylated form of the aglycon as compared to the cell of step a).

The selecting may be done in a number of ways according to the art. For instance in a micro titer assay where each well comprises a sample of a specific cell and there is measured amounts of the glycosylated form of the aglycon. There are numerous other ways of doing this according to the general knowledge of the skilled person.

Example 8 describes how this method is used to make an *Arabidopsis thaliana* plant capable of producing increased mg of dhurrin per gram of fresh weight. The starting cell of step a) is the *Arabidopsis thaliana* transgenic cell described in Tattersall, D B et al, Science (2001) 293:1826-8. As explained above the *Arabidopsis thaliana* transgenic cell comprises the entire pathway for synthesis of the cyanogenic glucoside dhurrin. It was demonstrated that the transgenic *Arabidopsis thaliana* plant was capable of producing 4 mg of dhurrin per gram of fresh weight. After performing the method as described in example 8 an *Arabidopsis thaliana* transgenic cell is selected in step c) that produces more than 6 mg of dhurrin per gram of fresh weight.

Without being limited to theory, it is believed to be the first time that a plant has been provided that is capable of producing more than 4 mg per gram of fresh weight of a glycosylated form of a low molecular weight organic aglycon compound.

Accordingly, as said above a fifth aspect of the invention relates to a plant capable of producing more than 5 mg per gram of fresh weight of a glycosylated form of a low molecular weight organic aglycon compound, (i) wherein the low molecular weight organic aglycon compound has a molecular weight from 50 to 3000.

Preferably, the plant is capable of producing more than 6 mg per gram of fresh weight of a glycosylated form of a low molecular weight organic aglycon compound, more preferably the plant is capable of producing more than 8 mg per gram of fresh weight of a glycosylated form of a low molecular weight organic aglycon compound. Preferably, the plant produces from 5 mg to 40 mg per gram of fresh weight of a glycosylated form of a low molecular weight organic aglycon compound.

Preferably, the plant is a transgenic plant.

EXAMPLES

General Molecular Biology Methods

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for *Bacillus*". John Wiley and Sons, 1990).

Enzymes for DNA manipulations were used according to the specifications of the suppliers.

Example 1

Analysis of Increased Tolerance to Vanillin in Microorganisms Expressing a UDPG-Glucosyl Transferase Vanillin sensitivity is determined in a number of microorganisms. The microorganisms includes the *Escherichia coli* strains DH5-alpha, TOP10, JM109 and K01418; the *Pseudomonas fluorescens* strains DSM 50091, DSM 50108 and DSM 50124; the *Bacillus subtilis* strain DSM 704; and the *Corynebacterium glutamicum* strain DSM 20300. The microorganisms also include strains of *Saccharomyces cerevisiae, S. uvarum, S. bayanus, S. paradoxus, S. kudriavzevii, S. mikatae, S. cariocanus, S. servazzii, S. castellii, S. kluyverii, Kluyveromyces lactis, Zygosaccharomyces fermentatii, Torulaspora delbruekii, Debaromyces orientalis* and *Schizosaccharomyces pombe.*

The minimum inhibitory concentration of vanillin is determined by the two-fold serial dilution assay (Hufford et al, 1975, J Pharm Sci 4: 789). Furthermore, the concentration of vanillin necessary to inhibit growth by more than 50% is determined. Once the sensitivity of vanillin has been determined in the various bacterial and yeast strains a few of these are selected in order to obtain microbial strains displaying a broad range of vanillin sensitivity.

The selected strains are transformed with a UDPG-glucosyl transferase gene, e.g. *Sorghum bicolor* UDPG-glucosyl transferase UGT85B1 (Jones et al, 1999, J Biol Chem 274: 35483), *Arabidopsis thaliana* UDPG-glucosyl transferase UGT89B1 (Lim et al, 2002, J Biol Chem 277: 586) and *Rauvolfia serpentina* arbutin synthase (Arend et al, 2001, Biotechnol Bioeng 76: 126).

For expression of UDPG-glucosyl transferase in *E. coli*, the IPTG-inducible expression vectors pSP19g10L, pKK223-3 and pET101D/Topo are employed. In addition, the newly constructed *E. coli* expression vectors using constitutive *E. coli* glycolytic gene promoters are used. For expression in *P. fluorescens*, the BHR expression vector pYanni3 are used. For expression of UDPG-glucosyl transferase in yeast, the genes are PCR amplified and inserted into plasmid pJH259, in which the genes are expressed from the constitutive and strong glycolytic TPII promoter. Alternatively, the TPII promoter is exchanged with a PCR-amplified MET25 promoter, which is repressible by methionine.

The UDPG-glucosyl transferase expressing microorganisms are subjected to analysis of their sensitivity to vanillin in the growth medium as described above. An increased tolerance to vanillin, determined as an increase in either the minimum inhibitory concentration or the concentration necessary to inhibit growth by more than 50%, means that transgenic UDPG-glucosyl transferase activity has converted some or most of the applied vanillin into vanillin glucoside, which is considerably less toxic.

Example 2

Identification of Glucosides in Microorganisms Expressing a UDPG-Glucosyl Transferase Microorganisms expressing a heterologous UDPG-glucosyl transferase are grown in medium containing appropriate levels of vanillin or ethylvanillin. The microorganisms are harvested and their content of glucosides is extracted in methanol or other suitable solvents. The presence of vanillin glucoside or ethylvanillin glucoside will be established and their levels will be quantified. The content of vanillin glucoside and ethylvanillin glucoside are compared in transgenic and non-transgenic microorganisms as well as in microorganisms grown in medium with and without vanillin or ethylvanillin.

The presence of increased amounts of vanillin glucoside or ethylvanillin glucoside in UDPG-glucosyl transferase expressing microorganisms grown in medium containing vanillin or ethylvanillin indicates that the aglucones are taken up and glucosylated by the transgenic organism.

Example 3

Increased Uptake and Turnover of ferulic Acid in Microorganisms Expressing a UDPG-Glucosyl Transferase Microorganisms capable of converting ferulic acid into vanillin are genetically modified to express a heterologous UDPG-glucosyl transferase. *Streptomyces setonii* strain ATCC 39116 is used for these studies since it has previously been employed for industrial production of vanillin from ferulic acid (Muheim & Lerch, 1999, Appl Microbiol Biotechnol 51: 456; Muheim et al, 1998, EP 0885968A1). Alternatively, *Pseudomonas putida* strain AN103 (Narbad & Gasson, 1998, Microbiol 144: 1397; Narbad et al, 1997, WO 97/35999), or *Amycolatopsis* sp. HR167 (Rabenhorst & Hopp, 1997, EP 0761817A2) are used. The microorganisms are transformed with the appropriate construct so as to express *Sorghum bicolor* UDPG-glucosyl transferase UGT85B1, *Arabidopsis thaliana* UDPG-glucosyl transferase UGT89B1 or *Rauvolfia serpentina* arbutin synthase.

The genetically modified microorganisms are grown in medium containing appropriate concentrations of ferulic acid. The uptake of ferulic acid is determined by following its concentration in the medium and its metabolic turnover are determined by analysis of the concentration of vanillin and vanillin glucoside in the microorganisms and the growth medium. These values are compared to similar analysis from experiments carried out with non-transgenic microorganisms.

An increased uptake of ferullic acid by microorganisms expressing heterologous UDPG-glucosyl transferase and their accumulation of vanillin glucoside demonstrate that the glucosyl transferase has increased the conversion of ferulic acid into vanillin, which is then subsequently converted into vanillin glucoside.

Example 4

Increased Yield of Vanillin Through Deglucosylation of Vanillin Glucoside Produced in Microorganisms Expressing a UDPG-Glucosyl Transferase Microorganisms capable of converting ferulic acid into vanillin are transformed with a gene encoding a UDPG-glucosyl transferase and are grown in the presence of ferulic acid. The concentration of ferulic acid in the growth medium is monitored and kept at constant level in order to compensate for the amount taken up by the microorganisms and used for the synthesis of vanillin. After a period of several days, vanillin is extracted from the microorganisms and quantified. In addition, vanillin glucoside will be extracted and converted into vanillin through deglucosylation by beta-glucosidase activity in vitro. The amount of recovered vanillin will be quantified.

Similar experiments and quantification of vanillin synthesised as an end product as well as vanillin recovered from in vitro deglucosylation of vanillin glucoside are performed in non-transformed microorganisms.

A greater amount of total vanillin extracted and recovered from UDPG-glucosyl transferase expressing microorganisms as compared to non-transformed microorganisms demonstrates that the presence of a heterologous UDPG-glucosyl transferase can lead to more ferulic acid being channeled into the synthesis of vanillin and its glucosylated form, from which vanillin can later be recovered. Consequently, total yield of vanillin can be increased through expression of a UDPG-glucosyl transferase.

Example 7

Facilitating Purification of an Organic Molecule by Glucosylation

The cell used in this example is the *E. coli* cell of Example 13, capable of producing vanillin glucoside.

In continuous fermentation the fermentor is inoculated with media for growth and the fermentation is started under aerobic conditions.

The first 12-18 hours is run for cell growth and after 12-18 hours the fermentor is fed with glucose for production of vanillin glucoside. During this part of the fermentation the growth rate is linear and it is anticipated that the limiting factor is the solubility of vanillin glucoside. From other corresponding glucosides it is known that the solubility is app. 100 g/l at STP and increases at higher temperatures.

After approximately 30 hours the high concentration is reached and harvesting is started. The cells are separated and recycled to the fermentor.

The supernatant is either concentrated to the limit of vanillin glucoside solubility or directly passed through a column with beta-glucosidase. The supernatant is re-circulated to the fermentor. If other products should be present, the vanillin solution can be passed over a cleaning column before recirculation. It is anticipated to have a row of columns where one is being used in the process while the others are cleaned and regenerated.

The product is recovered as crystals from the enzymatic treatment. In order to decrease the amount of re-circulated vanillin the temperature is lowered in connection with enzyme treatment.

Example 9

Vanillin Sensitivity of Various Strains of *E. coli*

The three different *E. coli* strains TOP10, JM109, and KO1418 were grown for 18 hours in the appropriate media, after which serial dilutions in growth medium (dilution factors 1, 1/100, 1/10000 and 1/1000000) were made. Droplets of these cell suspensions were applied to Petri dishes containing solid LB growth medium with various concentrations of vanillin, and the plates were incubated at the appropriate growth temperature for 24 hours (*E. coli*), after which they were photographed. The percentual (w/v) concentration of vanillin at which growth of a given microorganism at the 1/10000 dilution was not detectable, and at which growth at the 1/100 dilution was severely inhibited, was recorded. This number constituted the STV (Sensitivity To Vanillin) level. The STV numbers for the different microorganisms studied can be seen in Table 9.1.

TABLE 9.1

Vanillin sensitivity for various *E. coli* strains on solid growth medium

| Strain | Genotype | STV |
| --- | --- | --- |
| TOP10 | F– mcrA Delta (mrr-hsdRMS-mcrBC) Phi80lacZ Delta-M15 Delta-lacX74 recA1 deoR araD139 Delta (ara-leu)7697 galU galK rpsL (StrR) endA1 nupG | 0.12 |
| JM109 | F'traD36 lacIq Delta (lacZ) M15 proA+B+/e14– (McrA–) Delta (lac-proAB) thi gyrA96 (NalR) endA1 hsdR17 (rK– mK–) relA1 supE44 recA1 | 0.14 |
| KO1418 | F– Delta (codB-lacI) 3 relA1? bglA677::Tn10 spoT1 bglB676::Lambda-lacZ bglGo-67 thi-1 | 0.18 |

Example 10

PCR Amplification of *S. bicolor* UGT85B1, *A. thaliana* UGT89B1 and *R. serpentina* Arbutin Synthase (AS) Genes Roche Pwo polymerase and a DNA Engine Thermocycler were used for all PCR amplifications. The oligonucleotides referred to in the text are described in Table 10.1.

TABLE 10.1

Oligonucleotides used in this study

| Oligo JH# | Name | Sequence (5'-3') |
|---|---|---|
| 1 | SB_GT_KK_F | ATTAGAATTCATGGGCAGCAACGCGCCGCCGCCG SEQ ID NO 1 |
| 2 | SB_GT_KK_R | ATTAAAGCTTTTACTGCTTGCCCCCGACCAGCAG SEQ ID NO 2 |
| 3 | SB_GT_pET_F | CACCATGGGCAGCAACGCGCCGCCGGCG SEQ ID NO 3 |
| 4 | SB_GT_pET_R | TTACTGCTTGCCCCCGACCAGCAG SEQ ID NO 4 |
| 5 | SB_GT_S_F1 | ATGGGCAGCAACGCGCCGCCT SEQ ID NO 5 |
| 6 | SB_GT_S_F2 | CGCAGCTGGCAGGGAGGCCGG SEQ ID NO 6 |
| 7 | SB_GT_S_F3 | GCCTCCGCCGGCCTCGCCGCC SEQ ID NO 7 |
| 8 | SB_GT_S_F4 | CAGACCACCAACTGCAGGCAG SEQ ID NO 8 |
| 9 | SB_GT_S_R1 | GAGAGGGAGAGGCCGTCGTCG SEQ ID NO 9 |
| 10 | AT_GT_KK-F | ATTAGAATTCATGAAAGTGAACGAAGAAACAAC SEQ ID NO 10 |
| 11 | AT_GT_KK-R | ATTAAAGCTTTTATTTGTTTAGTCCTAAACTAACGAC SEQ ID NO 11 |
| 12 | AT_GT_pET_F | ATGAAAGTGAACGAAGAAACAAC SEQ ID NO 12 |
| 13 | AT_GT_pET_R | TTATTTGTTTAGTCCTAAACTAACGAC SEQ ID NO 13 |
| 14 | AT_GT_S_F1 | ATGAAAGTGAACGAGGAAAAC SEQ ID NO 14 |
| 15 | AT_GT_S_F2 | GAATCCCTCGTTTCGATTTCT SEQ ID NO 15 |
| 16 | AT_GT_S_F3 | CTTGACGCACGTGAGGATAAC SEQ ID NO 16 |
| 17 | AT_GT_S_F4 | CCTGACACGGTGCCTGACCCG SEQ ID NO 17 |
| 18 | AT_GT_S_R1 | CGGAGGGGATTGAAGGGTGGG SEQ ID NO 18 |
| 19 | AS_GT_EC_KK_F | ATTAGAATTCATGGAACATACCCCGCACATT SEQ ID NO 19 |
| 20 | AS_GT_EC_KK_R | ATTAGAATTCTTATGTACTGGAAATTTTGTTC SEQ ID NO 20 |
| 21 | AS_GT_EC_pET_F | CACCATGGAACATACCCCGCACATT SEQ ID NO 21 |
| 22 | AS_GT_EC_pET_R | TTATGTACTGGAAATTTTGTTC SEQ ID NO 22 |
| 23 | AS_GT_S_F1 | ATGGAGCATACACCTCACAT SEQ ID NO 23 |
| 24 | AS_GT_S_F2 | GACGGCCATGTGCCTGTCTC SEQ ID NO 24 |
| 25 | AS_GT_S_F3 | GGGGCAGTCTCCCATAATCA SEQ ID NO 25 |
| 26 | AS_GT_S_F4 | AGGGTCTTAAAGTGGCCCTG SEQ ID NO 26 |
| 27 | AS_GT_S_R1 | TACGGGTCTCTATCCTAACA SEQ ID NO 27 |
| 28 | Pfba_F | ATTAGAATTCAAAAATCACAGGGCAGGGAAAC SEQ ID NO 28 |
| 29 | Pfba_R | ATTAGGCGCGCCTCTAGAGTCTCTTGTCCTGTATCGTCGGG SEQ ID NO 29 |
| 30 | PpfkA_F | ATTAGAATTCTCAGTATAAAAGAGAGCCAGAC SEQ ID NO 30 |
| 31 | PpfkA_R | ATTAGGCGCGCCTCTAGAGACTACCTCTGAACTTTGGAAT SEQ ID NO 31 |
| 32 | PgapA_F | ATTAGAATTCTTGCTCACATCTCACTTTAATC SEQ ID NO 32 |
| 33 | PgapA_R | ATTAGGCGCGCCTCTAGAATATTCCACCAGCTATTTGTTA SEQ ID NO 33 |
| 34 | PtpiA_F | ATTAGAATTCCAAAAAGCAAAGCCTTTGTGCC SEQ ID NO 34 |
| 35 | PtpiA_R | ATTAGGCGCGCCTCTAGATTTAATTCTCCACGCTTATAAG SEQ ID NO 35 |
| 36 | TcysB_F | ATTAGGCGCGCCGGATCCTTTCTTGCGTTATTTTCGGCACC SEQ ID NO 36 |
| 37 | TcysB_R | ATTAAAGCTTGAAAAACCGCCAGCCAGGCTTT SEQ ID NO 37 |
| 38 | SB_GT_EC_NP_F | ATTATCTAGAATGGGCAGCAACGCGCCGCCGCCG SEQ ID NO 38 |
| 39 | SB_GT_EC_NP_R | ATTAGGATCCTTACTGCTTGCCCCCGACCAGCAG SEQ ID NO 39 |
| 40 | AT_GT_EC_NP_F | ATTATCTAGAATGAAAGTGAACGAAGAAACAAC SEQ ID NO 40 |
| 41 | AT_GT_EC_NP_R | ATTAGGATCCTTACCACCGTTCTATCTCCATCTTC SEQ ID NO 41 |
| 42 | RS_GT_EC_NP_F | ATTATCTAGAATGGAACATACCCCGCACATT SEQ ID NO 42 |
| 43 | RS_GT_EC_NP_R | ATTAGGATCCTTATGTACTGGAAATTTTGTTC SEQ ID NO 43 |

UGT85B1, UGT89B1 and AS for IPTG-Controlled Expression in *E. coli*

For amplification of UGT85B1 for use in the *E. coli* vector pKK223-3 (Amersham-Pharmacia Biotech), the oligonucleotides JH#1 and JH#2 (Table 10.1) were used, with the plasmid pSP19g10L-UGT85B1 (Jones et al., 1999, J Biol Chem 274: 35483) as template for the reaction. The reaction conditions employed were 94° C., 2 min., 1 cycle, 94° C., 30 sec., gradient 50-60° C., 1 min., 72° C., 2 min., 30 cycles, followed by 72° C., 7 min., 1 cycle. The reaction contained 5% DMSO. Reaction samples containing a fragment of the expected size of 1.5 kb were combined, and used for ligation into the pCR-Blunt II-Topo vector. Clones containing EcoRI inserts of 1.5 kb were sequenced with the primers JH#5-9. A clone with a correct DNA sequence was identified and named pJH400. The UGT85B1 ORF was liberated from pJH400 with EcoRI-HindIII (these restriction sites were included at the 5'-termini of the primers) and inserted in an EcoRI-HindIII digested pKK223-3 plasmid. A clone with a correct UGT85B1 insert was identified and named pJH401.

For amplification of UGT85B1 for use in the *E. coli* vector pET101-D/Topo, an identical PCR reaction was performed, only using the primers JH#3 and 4. The same PCR program was employed, and a fragment of the correct size of 1.5 kb was directionally inserted in the expression vector pET101-D/Topo. The inserts of several clones were sequenced using primers JH#5-9. One correct clone was named pJH402.

For amplification of UGT89B1 for use in the *E. coli* vector pKK223-3, the oligonucletides JH#10 and JH#11 (Table 10.1) were used, with genomic *Arabidopsis thaliana* DNA (var. *Columbia* Col-0) as template for the reaction. The reaction conditions employed were 94° C., 2 min., 1 cycle, 94° C., 30 sec., gradient 50-60° C., 1 min., 72° C., 2 min., 30 cycles, followed by 72° C., 7 min., 1 cycle. Reaction samples containing a fragment of the expected size of 1.4 kb were combined, and used for ligation into the pCR-Blunt II-Topo vector. Clones containing EcoRI inserts of 1.4 kb were sequenced with the primers JH#14-18. A clone with a correct DNA sequence was identified and named pJH462. The UGT89B1 ORF was liberated from pJH462 with EcoRI-HindIII (these restriction sites were included at the 5'-termini of the primers) and inserted in an EcoRI-HindIII digested pKK223-3 plasmid. A clone with a correct UGT89B1 insert was identified and named pJH463.

For amplification of UGT89B1 for use in the *E. coli* vector pET101-D/Topo, an identical PCR reaction was performed, only using the primers JH#12 and 13. The same PCR program was employed, and a fragment of the correct size of 1.4 kb was directionally inserted in the expression vector pET 101-D/Topo. The inserts of several clones were sequenced using primers JH#14-18. One correct clone was named pJH406.

For amplification of AS for use in the *E. coli* vector pKK223-3, the oligonucletides JH#19 and JH#20 (Table 10.1) were used, with the plasmid pQE60-AS (Arend et al., 2001, Biotechnol Bioeng 76: 126) as template for the reaction. The reaction conditions employed were 94° C., 2 min., 1 cycle, 94° C., 30 sec., gradient 48-55° C., 1 min., 72° C., 2 min., 30 cycles, followed by 72° C., 7 min., 1 cycle. Reaction samples containing a fragment of the expected size of 1.4 kb were combined, and used for ligation into the pCR-Blunt II-Topovector. Clones containing EcoRI inserts of 1.5 kb were sequenced with the primers JH#23-27. A clone with a correct DNA sequence was identified and named pJH409. The AS ORF was liberated from pJH409 with EcoRI (EcoRI sites were included at the 5'-termini of both primers) and inserted in an EcoRI digested pKK223-3 plasmid. A clone with a correct AS insert in the correct orientation was identified and named pJH410.

For amplification of AS for use in the *E. coli* vector pET101-D/Topo, an identical PCR reaction was performed, only using the primers JH#21 and 22. The same PCR program was employed, and a fragment of the correct size of 1.4 kb was directionally inserted in the expression vector pET101-D/Topo. The inserts of several clones were sequenced using primers JH#23-27. One correct clone was named pJH411.

UGT85B1, UGT89B1 and AS for Constitutive Expression in *E. coli*

A series of tailored expression systems for UGT85B1 and AS were constructed in which the glucosyl transferase genes were controlled by one of four glycolytic *E. coli* gene promoters: fba (primers JH#28 and 29), pfkA (JH#30 and 31), tpiA (JH# 32 and 33) and gapA (JH#34 and 35) promoters, and all by the *E. coli* cysB terminator (primers JH#27 and 28) sequences. All constructions were based on the following scheme: The promoter fragment was PCR amplified from *E. coli* DH5α genomic DNA, inserted BamHI-AscI (these sites were present in the primers) in pKOL30 (Olesen et al., 2000, Yeast 16: 1035). In the resulting construct the cysB fragment was then inserted AscI-HindIII (sites present in primers). Finally, in the resulting construct, PCR amplified UGT85B1 (primers JH#38 and 39), UGT89B1 (primers JH#40 and 41) or AS (JH# 42 and 43) were then inserted XbaI-EcoRI (these sites were present inside the AscI sites in the 3'-end primer used for promoter amplification and in the 5'-end primer used for the terminator amplification, as well as in the primers used for amplification of the UGT and AS genes).

The PCR reaction conditions employed were 94° C., 2 min., 1 cycle, 94° C., 30 sec., 55° C., 1 min. (for promoter and terminator fragments, as well as UGT fragments) or 48° C., 1 min. (for AS fragment), 72° C., 2 min., 30 cycles, followed by 72° C., 7 min., 1 cycle. For amplification of UGT85B1, 5% DMSO was included. Reaction samples containing a fragment of the expected sizes were combined, gel purified and used for cloning experiments as described above.

The resulting plasmids were pJH430 (fba-UGT85B1), pJH431 (pfkA-UGT85B1), pJH432(gapAA-UGT85B1), pJH433 (tpiA-UGT85B1), pJH434 (fba-UGT89B1), pJH435 (pfkA-UGT89B1), pJH436 (gapA-UGT89B1), pJH437 (tpiA-UGT89B1), pJH438 (fba-AS), pJH439 (pfkA-AS), pJH440 (gapA-AS) and pJH441 (tpiA-AS).

Example 11

Vanillin Detoxification by Expression of UGT or AS Genes *E. coli*

The *E. coli* strains TOP10, JM109, and KO1418 were all transformed with the constructed plasmids pJH401, pJH402, pJH411 and pJH412, and pKK223-3 as control, employing standard transformation protocols. Transformants were selected for ampicilin resistance, and two transformants of each *E. coli* strain with each plasmid were kept for expression experiments. The *E. coli* transformants were inoculated from plate cultures into 2 ml liquid growth medium (LB medium containing ampicilin at 100 μg/ml), and allowed to grow for 20 hours at 37° C. The precultures were diluted 100 times $10^4$ times and $10^6$ times in growth medium, and 4 μl droplets of these cell suspensions were applied to the surface of Petri dishes containing solid LB-ampicilin medium containing varying concentrations of vanillin (based on the STV determinations described above), and without or with (to induce gene expression) 1 mM isopropyl thiogalactoside (IPTG). The plates were incubated at 37° C. for 24 hours, after which growth on the various concentrations of vanillin was monitored and recorded. The results are summarized in Table 11.1.

TABLE 11.1

Effect of IPTG-induced expression of S. bicolor UGT85B1 or R. serpentina AS on the toxicity of vanillin on three different strains of E. coli.

|  | % Vanillin | | | | | IPTG |
| --- | --- | --- | --- | --- | --- | --- |
| E. coli strain | 0% | 0.08% | 0.12% | 0.16% | 0.2% | induction |
| JM109 [pKK223-3] | ++ | ++ | ++ | − | − | No |
|  | ++ | ++ | ++ | − | − | Yes |
| JM109 [pJH401] | ++ | ++ | ++ | − | − | No |
|  | ++ | ++ | ++ | − | − | Yes |
| JM109 [pJH402] | ++ | ++ | ++ | + | − | No |
|  | ++ | ++ | ++ | ++ | − | Yes |
| JM109 [pJH410] | ++ | ++ | ++ | ++ | − | No |
|  | ++ | ++ | ++ | + | − | Yes |
| KO1418 [pKK223-3] | ++ | ++ | ++ | − | − | No |
|  | ++ | ++ | ++ | ++ | − | Yes |
| KO1418 [pJH401] | ++ | ++ | ++ | − | − | No |
|  | ++ | ++ | ++ | ++ | − | Yes |
| KO1418 [pJH402] | ++ | ++ | ++ | + | − | No |
|  | ++ | ++ | ++ | ++ | − | Yes |
| KO1418 [pJH410] | ++ | ++ | ++ | ++ | − | No |
|  | ++ | ++ | ++ | ++ | ++ | Yes |

−: No growth;
+: weak growth;
++: good growth.

From these experiments we conclude that expression of S. bicolor UGT85B1 is possible in some E. coli strains and with some types of IPTG-inducible gene promoters, and that a stronger vanillin detoxification can be obtained by expression of the AS gene, but only in an E. coli strain in which the phospho-α-glucosidase encoding bgl locus has been inactivated (strain KO1418).

For experimentation with constitutive expression of UGT85B1 and AS, the E. coli strains JM109, and K01418 were transformed with the constructed plasmids pJH 430, pJH431, pJH432, pJH433, pJH434, pJH435, pJH436, pJH437, pJH438, pJH439, pJH440, and pJH441, and pKOL30 as control, employing standard transformation protocols. Transformants were selected for ampicilin resistance, and two transformants of each E. coli strain with each plasmid were kept for expression experiments. The E. coli transformants were inoculated from plate cultures into 2 ml liquid growth medium (LB medium containing ampicilin at 100 µg/ml), and allowed to grow for 20 hours at 37° C. The precultures were diluted 100 times 10⁴ times and 10⁶ times in growth medium, and 4 µl droplets of these cell suspensions were applied to the surface of Petri dishes containing solid LB-ampicilin medium containing varying concentrations of vanillin (based on the STV determinations described above). The plates were incubated at 37° C. for 24 hours, after which growth on the various concentrations of vanillin was monitored and recorded. The results are summarized in Table 11.2. The results with E. coli strains JM109 and K01418 with the plasmids pJH430, pJH431, pJH432 and pJH433 are summarized in Table 10.2 below.

TABLE 11.2

Effect of constitutive expression of S. bicolor UGT85B1 or R. serpentina AS on the toxicity of vanillin on two different strains of E. coli.

|  | % Vanillin | | | |
| --- | --- | --- | --- | --- |
| E. coli strain | 0% | 0.08% | 0.12% | 0.16% |
| JM109 [pKOL30] | +++ | +++ | ++ | − |
| JM109 [pJH430] | +++ | +++ | +++ | ++ |
| JM109 [pJH431] | +++ | +++ | +++ | ++ |
| JM109 [pJH432] | +++ | +++ | +++ | + |
| JM109 [pJH433] | +++ | +++ | +++ | + |
| KO1418 [pKOL30] | +++ | +++ | ++ | + |
| KO1418 [pJH430] | +++ | +++ | +++ | +++ |
| KO1418 [pJH431] | +++ | +++ | +++ | +++ |
| KO1418 [pJH432] | +++ | +++ | +++ | + |
| KO1418 [pJH433] | +++ | +++ | +++ | +++ |

−: No growth;
+: weak growth;
++: growth;
+++: strong growth.

From these experiments we conclude that constitutive expression of glucosyl transferase genes in E. coli strain JM109 results in vanillin detoxification.

Example 12

Vanillin Glucoside (VG) Production in UGT85B1-, UGT89B1- or AS-Expressing Strains of E. coli Several E. coli strains expressing UGT85B1 or AS are tested for VG production by growth in liquid growth medium containing sublethal vanillin concentrations. The strains tested are JM109 and K01418 containing either of the following plasmids: pKK223-3, pJH401, pJH402, pJH406, pJH463, pJH410, pKOL30, pJH430, pJH431, pJH432, pJH433, pJH434, pJH435, pJH436, pJH437, pJH438, pJH439, pJH440 and pJH441.

The E. coli strains are inoculated over night at 37° C. in 2 ml LB medium containing 100 µg/ml ampicilin, and then diluted into 50 ml of the same growth medium (0.1 ml o.n. culture). Growth proceeds at 37° C. for 2 hours, and then IPTG is added to a concentration of 1 mM (0.5 ml 100 mM stock) to those strains containing IPTG-inducible UGT/AS-expression plasmids. The cell suspensions are then incubated at 28° C. for 1 hour, after which vanillin is added to a concentration of 0.05% (83 µl 30% ethanol stock). Growth then proceeds at 28° C. for 24 hours. Cultures are centrifuged LC-MS are employed to determine VG content in growth supernatant as well as lysates of cell pellets.

In another set of experiments, the same E. coli strains are grown in a similar way, but instead of vanillin, $^{14}$C-labelled vanillin (5 mCi of 50 mCi/mol) is added to the growing cultures, after which growth proceeds 28° C. for 1-24 hours. Supernatant samples are taken regularly as are cell samples. Cell lysates are produced and both growth supernatants and cell lysates are subjected to TLC (thin layer chromatography) as described (Jones et al., 1999, J Biol Chem 274: 35483). Employing autoradiography, radioactive vanillin and radioactive vanillin glucoside are detected.

By both of the above described analyses we are able to detect the presence of vanillin glucoside from cells expressing UGT or AS genes while no vanillin glucoside can be detected from growth of cells not expressing UGT or AS genes.

Example 13

Establishment of a De Novo Biosynthesis Pathway for the Supply of Vanillin to Microbial Expressed Glucosytransferases To establish a microbial pathway for the conversion of glucose to vanillin three heterologous enzymatic activities are expressed in the UDPG-glucosyltransferase expressing microorganism.

The first enzymatic activity is a 3-dehydroshikimate dehydratase, which "taps" out a distant vanillin precursor from the common aromatic amino acid biosynthetic pathway, namely 3-dehydroshikimate, and converts it to protocatechuic acid. 3-Dehydroshikimate dehydratase (3DHD) genes are known from *Neurospora crassa* (Ruthledge, 1984, Gene 32: 275), *Aspergillus nidulans* (Hawkins et al., 1985, Curr Genet 9: 305), *Podospora pauciseta* (GenBank accession # AL627362) and *Acinetobacter calcoaceticus* (Elsemore & Ornston, 1995, J Bacteriol 177: 5971). The next enzyme necessary is an aromatic carboxylic acid reductase (ACAR) that can convert protocatechuic acid to protocatechualdehyde. ATP-dependent ACAR activities are found in certain actinomycetes (*Nocardia* sp.) (use of *Nocardia* ACAR patented: Rosazza & Li, 2001, U.S. Pat. No. 6,261,814B1), in *Neurospora crassa* (Gross & Zenk, 1969, Eur J Biochem 8: 413) (use of ACAR enzyme preparation patented: Frost, 2002, U.S. Pat. No. 6,372,461B1) and in a range of basidiomycetes, socalled "white-rot" fungi, which are lignin degraders (e.g. *Trametes, Dichomitus, Bjerkandera* and *Pleurotus* ("Oyster mushroom") sp. (Hage et al., 1999, Appl Microbiol Biotechnol 52: 834). Data for a short N-terminal protein sequence from the *Nocardia* enzyme is available (Li & Rosazza, 1997, J Bacteriol 179: 3482), and the full nucleotide sequence of the gene has recently been published (He et al., 2004, Appl Env Microbiol 70: 1874-1881). Finally, a 3-O-methylation is necessary for the final conversion to vanillin. The candidate enzyme for this purpose is a strawberry S-adenosylmethiomme:furaneol O-methyltransferase gene (FaOMT) (Wein et al., 2002, Plant J 31: 755), as this enzyme rather specifically methylates protocatechuic aldehyde at the 3-0 position. Alternative methylases include aspen (Bugos et al., 1991), Plant Mol Biol 17: 1203), almond (Garcia-Mas et al., 1995, Plant Phys 108:1341) and *Vanilla planifolia* (Pak et al., 2004, Plant Cell Rep: 11) OMTs. To avoid the accumulation of toxic intermediates the first gene expressed in a functional UGT-expressing microbial strain will be the methyl transferase gene. When this has been seen to work (i.e. producing vanillin glucoside from protocatechualdehyde), the aldehyde dehydrogenase is introduced, etc., until the intrinsic 3-dehydroshikimate-producing pathway is reached.

The strawberry FaOMT gene is isolated by PCR, using *Fragraria* x *ananassa* (strawberry) cDNA as template DNA. The cDNA is isolated from maturing *F. ananassa* var. *Elanta* using the QBiogene Fastprep Pro Green kit, and from the resulting total RNA preparation cDNA is synthesized employing the Invitrogen Superscript II Reverse transcriptase. This cDNA preparation is used for PCR amplification using FaOMT ORF-specific primers and Pwo polymerase (Roche Biochemicals). The resulting 1.1 kb FaOMT-containing DNA fragment is isolated and inserted between the XbaI and BamHI sites in the inducible *E. coli* expression vector pJH-X1, resulting in plasmid pJH-X2.

*E. coli* strain JH1, which corresponds to *E. coli* JM109 containing plasmid pJH430 (expressing UGT85B1 from the *E. coli* fba promoter) is transformed with plasmid pJH-X2. The resulting *E. coli* strain JH2 is grown in liquid LB growth medium to which protocatechualdehyde is added. Expression is induced. The culture supernatant of the outgrown culture is subjected to LC-MS, and vanillin glucoside is identified, meaning that a biosynthetic pathway that can convert protocatechualdehyde to vanillin glucoside has been established.

An ACAR gene that is effective in the conversion of protocatechualdehyde to vanillin is isolated in the following manner: cDNA is synthesized from total RNA extracted from either of the white rot fungi *Pleurotus ostreatus* or *Trametes gibbosa* by the use of Invitrogen Superscript II Reverse transcriptase. A phagemid cDNA library is produced using the Stratagene cDNA library construction system. DNA prepared from these libraries is used to isolate the 5'-region of white rot ACAR genes, taking advantage of the *Nocardia* ACAR nucleotide sequence information. The forward primer is identical to vector sequences present immediately upstream of the cDNA insertion location. The reverse primer is homologous to the area of the *Nocardia* ACAR gene that has the highest degree of evolutionary conservation, when the deduced amino acid sequence of this gene is compared to the deduced amino acid sequence of other putative ACAR genes found in the public sequence databases (by comparison with *Nocardia* ACAR). Several such primers with "base wobbling" at various nucleotide positions (i.e. degenerate primers) are used together with the forward primer in a PCR reaction using cDNA library DNA from either of the two libraries described above, and High Fidelity Plus polymerase (Roche Biocehmicals). Optimizing for annealing temperature and magnesium ion concentration, a PCR fragment of appr. 0.8 kb is isolated. By subcloning and nucleotide sequence analysis, this fragment is shown to encode the 5'-region of *P. ostreatus* or *T. gibbosa* ACAR. The obtained sequence information is used to define an ACAR-internal forward oligonucleotide primer that can be used together with a reverse primer identical to library vector sequences present distal to the 3'end of the cDNA inserts, to amplify the 3'-end of the *P. ostreatus* or *T. gibbosa* ACAR genes. After sequencing of the gene fragments thus isolated, a ACAR 3'-end specific oligonucleotide primer is defined, and employed together with a 5'-end specific primer, to obtain full length *P. ostreatus* or *T. gibbosa* ACAR, in a final PCR reaction. The cDNA insert of this clone is subjected to DNA sequencing analysis, and after confirmation of the ACAR gene sequence, the gene is inserted into the An ACAR gene that is effective in the conversion of protocatechualdehyde to vanillin is isolated in the following manner: cDNA is synthesized from total RNA extracted from either of the white rot fungi *Pleurotus ostreatus* or *Trametes gibbosa* by the use of Invitrogen Superscript II Reverse transcriptase. A phagemid cDNA library is produced using the Stratagene cDNA library construction system. DNA prepared from these libraries is used to isolate the 5'-region of white rot ACAR genes, taking advantage of the *Nocardia* ACAR nucleotide sequence information. The forward primer is identical to vector sequences present immediately upstream of the cDNA insertion location. The reverse primer is homologous to the area of the *Nocardia* ACAR gene that has the highest degree of evolutionary conservation, when the deduced amino acid sequence of this gene is compared to the deduced amino acid sequence of other putative ACAR genes found in the public sequence databases (by comparison with *Nocardia* ACAR). Several such primers with "base wobbling" at various nucleotide positions (i.e. degenerate primers) are used together with the forward primer in a PCR reaction using cDNA library DNA from either of the two libraries described above, and High Fidelity Plus polymerase (Roche Biocehmicals). Optimizing for annealing temperature and magnesium ion concentration, a PCR fragment of appr. 0.8 kb is isolated. By subcloning and nucleotide sequence analysis, this fragment is shown to encode the 5'-region of *P. ostreatus* or *T. gibbosa* ACAR. The obtained sequence information is used to define an ACAR-internal forward oligonucleotide primer that can be used together with a reverse primer identical to library vector sequences present distal to the 3' end of the cDNA inserts, to amplify the 3'-end of the *P. ostreatus* or *T. gibbosa* ACAR genes. After sequencing of the gene fragments thus isolated, a ACAR 3'-end specific oligonucleotide primer is defined, and employed together with a 5'-end specific primer, to obtain full length *P. ostreatus* or *T. gibbosa* ACAR, in a final PCR reaction. The cDNA insert of this clone is subjected to DNA sequencing analysis, and after confirmation of the ACAR gene sequence, the gene is inserted into the *S. cerevisiae* expression vector pJH413, resulting in plasmid pJH413-X1, the *E. coli* expression vector pJH-X2, resulting in plasmid pJH-X3.

*E. coli* strain JH1 (expressing UGT85B1) is transformed with plasmid pJH-X3. The resulting *E. coli* strain JH3 is grown in liquid LB growth medium to which protocatechuic acid is added. Expression is induced. The culture supernatant of the outgrown culture is subjected to LC-MS, and vanillin glucoside is identified, meaning that a biosynthetic pathway that can convert protocatechuic acid to vanillin glucoside has been established.

A 3DHD gene is isolated from *Podospora pauciseta* in the following manner: Genomic DNA is isolated from *P. pauciseta* using the QBiogene Fastprep DNA system, and the 3DHD gene is PCR amplified using this genomic DNA as template from the reaction with *P. pauciseta* 3DHD-specific primers, and the Pwo polymerase (Roche Biochemicals). The resulting 1.1 kb 3DHD gene fragment is inserted between the BamHI and XbaI sites of the *E. coli* expression vector pJH-X3, resulting in plasmid pJH-Van. *E. coli* strain JH1 (expressing UGT85B1) is transformed with plasmid pJH-Van.

The resulting *E. coli* strain JH4 is grown in liquid LB growth medium. Expression is induced. The culture supernatant of the outgrown culture is subjected to LC-MS, and vanillin glucoside is identified, meaning that a biosynthetic pathway that can convert glucose to vanillin glucoside has been established.

*E. coli* strain JM109 is now transformed with plasmid pJH-Van. The resulting strain, JH5 now contains a biosynthesis pathway for vanillin production from glucose, while strain JH4 contains a biosynthesis pathway for vanillin production in addition to the glucosyl transferase-encoding UGT85B1 gene. Strains JH4 and JH5 are both grown in liquid LB growth medium, and gene expression is induced. By the means described above we compare vanillin production in strain JH5 with vanillin glucoside production in strain JH4.

We observe that the *E. coli* strain containing a biosynthesis pathway for vanillin production in addition to a glucosyl transferase gene (strain JH4) produces higher amounts (on a molar basis) of vanillin glucoside as compared to the amounts of the corresponding vanillin aglucone.

Example 14

Establishment of a Vanillin De Novo Biosynthesis Pathway in *Saccharomyces cerevisiae* Yeast To establish a microbial pathway for the conversion of glucose to vanillin three heterologous enzymatic activities are obtained by molecular genetic techniques and expressed in *Saccharomyces cerevisiae*.

The first enzymatic activity is a 3-dehydroshikimate dehydratase, which "taps" out a distant vanillin precursor from the common aromatic amino acid biosynthetic pathway, namely 3-dehydroshikimate, and converts it to protocatechuic acid. 3-Dehydroshikimate dehydratase (3DHD) genes are known from *Neurospora crassa* (Ruthledge, 1984, Gene 32: 275), *Aspergillus nidulans* (Hawkins et al., 1985, Curr Genet 9: 305), *Podospora pauciseta* (GenBank accession # AL627362) and *Acinetobacter calcoaceticus* (Elsemore & Ornston, 1995, J Bacteriol 177: 5971). The next enzyme necessary is an aromatic carboxylic acid reductase (ACAR) that can convert protocatechuic acid to protocatechualdehyde. ATP-dependent ACAR activities are found in certain actinomycetes (*Nocardia* sp.) (use of *Nocardia* ACAR patented: Rosazza & Li, 2001, U.S. Pat. No. 6,261,814B1), in *Neurospora crassa* (Gross & Zenk, 1969, Eur J Biochem 8: 413) (use of ACAR enzyme preparation patented: Frost, 2002, U.S. Pat. No. 6,372,461B1) and in a range of basidiomycetes, so-called "white-rot" fungi, which are lignin degraders (e.g. *Trametes, Dichomitus, Bjerkandera* and *Pleurotus* ("Oyster mushroom") sp. (Hage et al., 1999, Appl Microbiol Biotechnol 52: 834). Data for a short N-terminal protein sequence from the *Nocardia* enzyme is available (Li & Rosazza, 1997, J Bacteriol 179: 3482), and the full nucleotide sequence of the gene has recently been published (He et al., 2004, Appl Env Microbiol 70: 1874-1881). Finally, a 3-O-methylation is necessary for the final conversion to vanillin. The candidate enzyme for this purpuse is a strawberry S-adenosylmethionine:furaneol O-methyltransferase gene (FaOMT) (Wein et al., 2002, Plant J 31: 755), as this enzyme rather specifically methylates protocatechuic aldehyde at the 3-O position. Alternative methylases include aspen (Bugos et al., 1991), Plant Mol Biol 17: 1203), almond (Garcia-Mas et al., 1995, Plant Phys 108:1341) and *Vanilla planifolia* (Pak et al., 2004, Plant Cell Rep: 11) OMTs.

The strawberry FaOMT gene was isolated by PCR, using *Fragraria* x *ananassa* (strawberry) cDNA as template DNA. The cDNA was isolated from maturing *F. ananassa* var. *Elanta* using the QBiogene Fastprep Pro Green kit, and from the resulting total RNA preparation cDNA was synthesized employing the Invitrogen Superscript II Reverse transcriptase. This cDNA preparation is used for PCR amplification using primers # 1 and # 2 (Table 14.1) and Pwo polymerase (Roche Biochemicals). The resulting 1.1 kb FaOMT-containing DNA fragment was isolated and inserted between the XbaI and BamHI sites of the *S. cerevisiae* expression vector pJH413, resulting in plasmid pJH471. The expression cassette (Ptpi1-FaOMT-Ttpi1) from pJH471 was then transferred NotI-NotI to the yeast integration vector pYC050 (Hansen et al., 2003, FEMS Yeast Res 4:323-327), resulting in the plasmid pJH494. Ten μg of plasmid pJH494 was linearized by restriction digestion with PsiI, and the resulting preparation was used to transform *S. cerevisiae* yeast strain JH1 to nourseothricin resistance, resulting in yeast strain FSC58.

A 3DHD gene was isolated from *Podospora pauciseta* in the following manner: Genomic DNA was isolated from *P. pauciseta* using the QBiogene Fastprep DNA system, and the 3DHD gene was PCR amplified using this genomic DNA as template from the reaction with *P. pauciseta* 3DHD-specific primers #3 and #4 (Table 14.1), and the Pwo polymerase (Roche Biochemicals). The resulting 1.1 kb 3DHD gene fragment was inserted between the BamHI and XbaI sites of the *S. cerevisiae* expression vector pJH413, resulting in plasmid pJH485. The expression cassette (Ptpi1-3DSD-Ttpi1) from pJH485 was then transferred NotI-NotI to the yeast integration vector pYC070 (Hansen et al., 2003, FEMS Yeast Res 4:323-327), resulting in the plasmid pJH500. Ten μg of plasmid pJH500 was linearized by restriction digestion with Bsu36I, and the resulting preparation was used to transform *S. cerevisiae* yeast strain FSC58 to aureobasidin A resistance, resulting in yeast strain FSC67.

Synthetic complete yeast medium (50 ml, in 250 ml Ehrlenmeyer flasks) was inoculated with 50 μl of an over night culture of *S. cerevisiae* yeast strain FSC67 grown in the same medium, and the cultures allowed to grow at 30° C., 150 rpm shaking. One ml samples were taken at 24 h, and 500 μl of the cell-free growth supernatants precipited with an equal volume of 100% methanol. The resulting supernatants were subjected to HPLC analysis on an Agilent 1100 Series HPLC system, using a Zorbax SB-C18 column (3.5 μm), and an elution profile as follows: A gradient of $H_2O$ (pH 2.3 with $H_2SO_4$)-acetonitrile from 0 to 40% acetonitrile in 3 min., 40% acetonitrile for 1 min., a gradient from 40 to 80% acetonitrile for 2 min., and a gradient from 80 to 90% acetonitrile for 1 min., followed by 90% acetonitrile for 1 min. Protocatechuic acid and vanillic acid were detected by a diode array detector at 250 nm and 210 nm, and the following elution times were found: protocatechuic acid, 5.3 min, and vanillic acid, 5.9 min. The result of the experiment was that strain FSC67 was able to produce 0.3 g/l of protocatechuic acid and 0.01 g/l of vanillic acid, with no other precursor than glucose. It is anticipated that the FaOMT methyltransferase is much more efficient with protocatechuic aldehyde than with protocatechuic acid as substrate, and hence that incorporation of a carboxylic acid reductase (ACAR) enzyme in strain FSC67 will result in a much better conversion ratio of the formed protocatechuic acid as well as the de novo formation of vanillin from glucose.

An ACAR gene that is effective in the conversion of protocatechualdehyde to vanillin is isolated in the following manner: cDNA is synthesized from total RNA extracted from either of the white rot fungi *Pleurotus ostreatus* or *Trametes gibbosa* by the use of Invitrogen Superscript II Reverse transcriptase. A phagemid cDNA library is produced using the Stratagene cDNA library construction system. DNA prepared from these libraries is used to isolate the 5'-region of white rot ACAR genes, taking advantage of the *Nocardia* ACAR nucleotide sequence information. The forward primer is identical to vector sequences present immediately upstream of the cDNA insertion location. The reverse primer is homologous to the area of the *Nocardia* ACAR gene that has the highest degree of evolutionary conservation, when the deduced amino acid sequence of this gene is compared to the deduced amino acid sequence of other putative ACAR genes found in the public sequence databases (by comparison with *Nocardia* ACAR). Several such primers with "base wobbling" at various nucleotide positions (i.e. degenerate primers) are used together with the forward primer in a PCR reaction using cDNA library DNA from either of the two libraries described above, and High Fidelity Plus polymerase (Roche Biocehmicals). Optimizing for annealing temperature and magnesium ion concentration, a PCR fragment of appr. 0.8 kb is isolated. By subcloning and nucleotide sequence analysis, this fragment is shown to encode the 5'-region of *P. ostreatus* or *T. gibbosa* ACAR. The obtained sequence information is used to define an ACAR-internal forward oligonucleotide primer that can be used together with a reverse primer identical to library vector sequences present distal to the 3'end of the cDNA inserts, to amplify the 3'-end of the *P. ostreatus* or *T. gibbosa* ACAR genes. After sequencing of the gene fragments thus isolated, a ACAR 3'-end specific oligonucleotide primer is defined, and employed together with a 5'-end specific primer, to obtain full length *P. ostreatus* or *T. gibbosa* ACAR, in a final PCR reaction. The cDNA insert of this clone is subjected to DNA sequencing analysis, and after confirmation of the ACAR gene sequence, the gene is inserted into the *S. cerevisiae* expression vector pJH413, resulting in plasmid pJH413-X1. The NotI-NotI expression cassette is transferred to plasmid pYC040 (Hansen et al., 2003, FEMS Yeast Res 4:323-327), thus creating plasmid pJH413-X2. Ten μg of this plasmid is linearized using an appropriate restriction enzyme, and the preparation used to transform *S. cerevisiae* strain FSC67 to hygromycin B-resistance, thus creating yeast strain FSC67-X1.

Finally, synthetic complete medium (50 ml, in 250 ml Ehrlenmeyer flasks) is inoculated with 50 μl of an over night culture of *S. cerevisiae* yeast strain FSC67-X1 grown in the same medium, and the cultures allowed to grow at 30° C., 150 rpm shaking. One ml samples are taken at 0 h, 24 h, and 48 h, and 500 μl of the cell-free growth supernatants precipited with an equal volume of 100% methanol. The resulting supernatants are subjected to HPLC analysis. We observe the formation of significant amounts of vanillin from glucose as precursor with yeast strain FSC67-X1, and thus we conclude that a de novo vanillin biosynthesis pathway has been obtained.

TABLE 14.1

Oligonucleotides used in example 14.

| Oligo-nucleotide | 5'-3' Sequence |
|---|---|
| #1 SEQ ID 44 | ATTATCTAGAATGGGTTCCACCGGCGAGACTCAG |
| #2 SEQ ID 45 | ATTAGGATCCTCAGATCTTCTTAAGAAACTCAATG |
| #3 SEQ ID 46 | ATTATCTAGAATGCCTTCCAAACTCGCCATCACTTC |
| #4 SEQ ID 47 | ATTAGGATCCTTACAAAGCCGCTGACAGCGACAG |

Example 15

In Vivo Production of Vanillin Glucoside in *Saccharomyces cerevisiae* Yeast

A *S. cerevisiae* yeast strain expressing AS was tested for VG production by fed-batch growth in a 2 liter fermentor vessel, in liquid growth medium containing a sublethal vanillin concentration. The strain tested was JH6 (adh6 adh7) containing plasmid pJH413 (JH6 [pJH413]).

Plasmid pJH413 was constructed in the following way: The arbutin synthase (AS) gene was amplified using the oligonucleotide primers # 1 and # 2 (Table 15.1), with the plasmid pQE60-AS (Arend et al., 2001, Biotechnol Bioeng 76: 126) as template for the reaction. The reaction conditions employed were 94° C., 2 min., 1 cycle, 94° C., 30 sec., gradient 48-55° C., 1 min., 72° C., 2 min., 30 cycles, followed by 72° C., 7 min., 1 cycle. Reaction samples containing a fragment of the expected size of 1.4 kb were combined, and used for ligation into the pCR-Blunt II-Topo vector. Clones containing EcoRI inserts of 1.5 kb were sequenced with the primers JH#23-27 (Table 10.1 in Example 10). A clone with a correct DNA sequence was identified and from this plasmid the AS ORF was liberated XbaI and BamHI (such sites were included at the 5'-termini of the PCR amplification primers) and inserted into the corresponding sites of the yeast expression vector pJH259 (derivative of plasmid pJH235; Hansen et al., 2003, FEMS Yeast Res 2:137-149). A clone with a correct AS insert was identified and named pJH413.

Strain JH6 was transformed with plasmid pJH413 and inoculated for 48 h at 30° C. in 2 ml SC-ura medium containing, and then all of this culture is diluted into 1.8 liter of the same growth medium. The culture was grown with oxygenation for 24 hours, after which more glucose (20 g/l) was added, along with 5 mM of vanillin. At T=48 h another 10 g/l of glucose and 5 mM vanillin was added. A 10 ml sample was taken at T=72 h, and the cellular as well as extracellular content of vanillin and its derivatives was extracted with hot ethanol. The resulting extract was concentrated ten times under vacuum, and the concentrated culture extract subjected to LC-MS analysis. A part of the concentrated culture sample was treated with almond β-glucosidase, and then subjected to LC-MS analysis. The culture content of the β-glucosides of vanillin, vanillic acid and vanillyl alcohol was determined by LC-MS analysis.

The conclusion is that vanillin glucoside can be formed in vivo in Saccharomyces cerevisiae by the glucosylation of vanillin. As vanillin glucoside is much less toxic to microbial organisms than is the aglycon vanillin, we conclude that expression of appropriate UDP-glucose glycosyltransferases in Saccharomyces yeast allows for overproduction of vanillin.

TABLE 15.1

Oligonucleotides used in example 15.

| Oligonucleotide | 5'-3' Sequence |
|---|---|
| #1 SEQ ID 48 | ATTATCTAGAATGGAACATACACCTCACATT |
| #2 SEQ ID 49 | ATTAGGATCCTTATGTACTGGAAATTTTGTTC |

Example 16

Overproduction of Protocatechuic Acid in Saccharomyces cerevisiae by Expression of the Arabidopsis thaliana UGT89B1 Glucosyltransferase A Saccharomyces cerevisiae strain producing protocatechuic acid due to expression of the Podospora pauciseta 3-dehydroshikimate dehydratase (3DSD) gene was constructed, and used to show overproduction of protocatechuic acid due to expression of the Arabidopsis thaliana UGT89B1 glucosyltransferase.

S. cerevisiae strain JH1 was transformed with linearized plasmid pJH500 (as described in example 14) in order to allow for overexpression of the P. pauciseta 3-dehydroshikimate dehydratase, in the manner described in Example 14. The resulting yeast strain was denoted FSC59, and this strain was used for transformation with the UGT89B1 yeast expression plasmid pJH468.

Plasmid pJH468 was constructed in the following way: The UGT89B1 gene was PCR amplified using the oligonucleotides #1 and #2 (Table 16.1), with genomic Arabidopsis thaliana DNA (var. Columbia Col-0) as template for the reaction. The reaction conditions employed were 94° C., 2 min., 1 cycle, 94° C., 30 sec., gradient 50-60° C., 1 min., 72° C., 2 min., 30 cycles, followed by 72° C., 7 min., 1 cycle. Reaction samples containing a fragment of the expected size of 1.4 kb were combined, and used for ligation into the pCR-Blunt II-Topo vector. Clones containing EcoRI inserts of 1.4 kb were sequenced with the primers JH#14-18 (Table 10.1, Example 10). A clone with a correct DNA sequence was identified and named pJH407. The UGT89B1 ORF was liberated from pJH407 with XbaI-BamHI (these restriction sites were included at the 5'-termini of the primers) and inserted in an XbaI-BamHI digested pJH259 plasmid. A clone with a correct UGT89B1 insert was identified and named pJH408. The URA3 selection marker of this plasmid was exchanged with the G418R selection marker (from plasmid pYC030, see Olesen et al., 2000, Yeast 16: 1035), and the yeast "origin of replication region" was removed by restriction digestion with FseI, followed by relegation, thus creating the yeast integration plasmid pJH468.

Ten μg of plasmid pJH468 was linearized by restriction digestion with PsiI, and the resulting preparation was used to transform S. cerevisiae yeast strain JFSC59 to nourseothricin resistance, resulting in yeast strain FSC60.

Synthetic complete yeast medium (50 ml, in 250 ml Ehrlenmeyer flasks) was inoculated with 50 μl of an over night culture of S. cerevisiae yeast strain JH1, FSC59 and FSC60 grown in the same medium, and the cultures allowed to grow at 30° C., 150 rpm shaking. One ml samples were taken at 48 h, and 500 μl of the cell-free growth supernatants precipitated with an equal volume of 100% methanol. The resulting supernatants were subjected to HPLC analysis on an Agilent 1100 Series HPLC system, using a Zorbax SB-C18 column (3.5 μm), and an elution profile as follows: A gradient of $H_2O$ (pH 2.3 with $H_2SO_4$)-acetonitrile from 0 to 40% acetonitrile in 3 min., 40% acetonitrile for 1 min., a gradient from 40 to 80% acetonitrile for 2 min., and a gradient from 80 to 90% acetonitrile for 1 min., followed by 90% acetonitrile for 1 min. Protocatechuic acid (PA) and protocatechuic acid-β-D-glucoside (PAG) were detected by a diode array detector at 250 nm and 210 nm, and the following elution times were found: protocatechuic acid, 5.4 min, and protocatechuic acid-β-D-glucoside, 4.7 min. The identity of PAG was confirmed by LC-MS analysis.

The result of the experiment was that strain FSC59 was able to produce 0.43 g/l of PA while strain FSC60 produced 0.28 g/l of PA and 0.69 g/l of PAG. When the sample from strain FSC60 were treated with almond β-glucosidase, the result was an increase in the PA content to 0.62 g/l acid, corresponding to an overproduction in strain FSC60 of PA of more than 40%, as compared to strain FSC59, in which the UGT89B1 glucosyl transferase was not expressed.

Thus we conclude that overproduction of protocatechuic acid is possible in yeast by the expression of A. thaliana UGT89B1 glucosyltransferase.

TABLE 16.1

Oligonucleotides used in example 16.

| Oligo-nucleotide | 5'-3' Sequence |
|---|---|
| #1 SEQ ID 50 | ATTATCTAGAATGAAAGTTAACGAAGAAAACAAC |
| #2 SEQ ID 51 | ATTAGGATCCTTACCACCGTTCTATCTCCATCTTC |

Example 17

Construction of *S. cerevisiae* Expression Vectors Containing *S. bicolor* CYP79A1, CYP71E1 and UGT85B1

In order to facilitate correct subcloning into the yeast expression vectors, the three genes were PCR amplified using primers with extensions which provided the DNA fragments with appropriate restrictions sites. CYP79A1 (using the plasmid CYP79A1PRT101 as template) was amplified with the primer pair SbC79F1S and SbC79R1E. CYP71E1 (using the plasmid CYP71E1pcDNAII as template) was amplified with the primer pair SbC71F1S and SbC71R1E. Finally, UGT85B1 (using the plasmid pcDNAII-UGT85B1 as template) was amplified with the primer pair SbUDPF1S and SbUDPR1E. Oligonucleotide primers are described in Table 17.1.

PCR was performed in the following way: Template DNA was used in the amount of 10 ng per reaction (volume of 50 μl). Primers and dNTPs were used in a final concentration of 1 μM. The three genes were amplified using 5 U of pfu polymerase (Stratagene) in a final MgSO$_4$ concentration of 2 mM. The following PCR conditions were used for the amplification: initially 95° C. for 5 minutes, thereafter 35 cycles of 95° C. for 45 seconds, Tm for 30 seconds and 72° C. for 90 seconds. Finally, 72° C. for 10 minutes. Tm for CYP79A1 was 62° C., Tm for CYP71E1 was 65° C. and Tm for UGT85B1 was 64° C.

The three amplified genes were initially cloned into pCR-Blunt 1'-TOPO (Invitrogen). Following transformation into *E. coli* strain DH5α and plasmid isolation using the QIAGEN system (QIAGEN), the integrity of the three genes was verified by DNA sequencing using appropriate sequencing primers.

Prior to subcloning into yeast expression vectors the above mentioned three genes were released from the TOPO vectors by cutting with the restriction enzymes EcoRI and SpeI followed by agarose gel-electrophoresis and DNA recovery using the QIAex system (Qiagen) according to manufactures instructions. Similarly, the yeast expressions vectors were cut with EcoRI and SpeI, treated with SAP and also recovered using the QIAex system.

Standard T4 DNA ligase (New England Biolabs) ligation was performed over night at 16° C., according to manufactures instructions. Following transformation into *E. coli* strain DH5α and plasmid isolation using the QIAGEN system according to manufactures instruction, the integrity of the yeast expression constructions was verified by cutting with appropriate restriction enzymes and gel-electrophoresis.

CYP79A1 was cloned into the following plasmid vectors (Mumberg et al. 1995, Gene 156: 119-122): p416-GPD (resulting in p#33A), p426-GPD (resulting in p#34A), p416-TEF (resulting in p#41A) and p426-TEF (resulting in p#42A). CYP71E1 was cloned into the following vectors: p413-GPD (resulting in p#27A), p423-GPD (resulting in p#28A), p413-TEF (resulting in p#35A) and p413-ADH (resulting in p#43A). UGT85B1 was cloned into the vector p415-GPD (resulting in p#S31B).

TABLE 17.1

Oligonucleotide sequence for primers used for cloning.

| Name | Primer sequence |
|---|---|
| SbC79F1S | 5'-agcactagtatggcgacaatggaggtagaggcc-3' SEQ ID 52 |
| SbC79R1E | 5'-agcgaattctcagatggagatggacgggtagagg-3' SEQ ID 53 |
| SbC71F1S | 5'-agcactagtatggccaccaccgccacccgcagctcc-3' SEQ ID 54 |
| SbC71R1E | 5'-agcgaattcctaggcggcgcggcggttcttgtatttgg-3' SEQ ID 55 |
| SbUDPR1E | 5'-agcgaattctcactgcttgccccgaccagcagc-3' SEQ ID 56 |
| SbUDPF1S | 5'-agcactagtatgggcagcaacgcgccgcctcc-3' SEQ ID 57 |

Example 18

Construction of *S. cerevisiae* Strains Expressing *S. bicolor* CYP79A1, CYP71E1 and UGT85B1 and of Strains Containing Mock Plasmids Standard yeast transformation by electroporation (Becker and Guarente, 1991, Methods in Enzymology 194: 182-187) was done in the yeast strain BY4741 (mata his3D1 leu2D0 met15D0 ura3D0) (EUROSCARF).

The following yeast strains (expressing the three *S. bicolor* genes) were constructed by transformation with the above mentioned plasmid and selected on SC-His,Ura,Leu media:

Y0109 by transformation of BY4741 with the plasmids p#27A, p#33A and p#S31B.

Y0113 by transformation of BY4741 with the plasmids p#28A, p#34A and p#S31B.

Y0117 by transformation of BY4741 with the plasmids p#35A, p#41A and p#S31B.

Y0121 by transformation of BY4741 with the plasmids p#43A, p#42A and p#S31B.

The following yeast strains (containing mock plasmids) were constructed by transformation with the above mentioned plasmid and selected on SC-His,Ura,Leu media:

Y0084 by transformation of BY4741 with the plasmids p413-GPD, p416-GPD and p415-GPD. Y0085 by transformation of BY4741 with the plasmids p423-GPD, p426-GPD and p415-GPD. Y0086 by transformation of BY4741 with the plasmids p413-TEF, p416-TEF and p415-GPD. Y0087 by transformation of BY4741 with the plasmids p413-ADH, p426-TEF and p415-GPD.

The following yeast strains (expressing the two *S. bicolor* genes CYP79A1 and CYP71E1) were constructed by transformation with the above mentioned plasmid and selected on SC-His,Ura media:

Y0091 by transformation of BY4741 with the plasmids p#27A and p#33A.

Y0092 by transformation of BY4741 with the plasmids p#28A and p#34A.

Y0093 by transformation of BY4741 with the plasmids p#35A and p#41A.

Y0094 by transformation of BY4741 with the plasmids p#43A and p#42A.

The following yeast strains (containing mock plasmids) were constructed by transformation with the above mentioned plasmid and selected on SC-His,Ura media:

Y0071 by transformation of BY4741 with the plasmids p413-GPD and p416-GPD.

Y0072 by transformation of BY4741 with the plasmids p423-GPD and p426-GPD.

Y0073 by transformation of BY4741 with the plasmids p413-TEF and p416-TEF.

Y0074 by transformation of BY4741 with the plasmids p413-ADH and p426-TEF

The following yeast strains (expressing the two *S. bicolor* genes CYP79A1 and UGT85B1) were constructed by transformation with the above mentioned plasmid and selected on SC-Ura,Leu media:

Y0103 by transformation of BY4741 with the plasmids p#33A and p#S31B.

Y0104 by transformation of BY4741 with the plasmids p#34A and p#S31B.

Y0105 by transformation of BY4741 with the plasmids p#41A and p#S31B.

Y0106 by transformation of BY4741 with the plasmids p#42A and p#S31B.

The following yeast strains (containing mock plasmids) were constructed by transformation with the above mentioned plasmid and selected on SC-Ura, Leu media:

Y0078 by transformation of BY4741 with the plasmids p416-GPD and p415-GPD.

Y0079 by transformation of BY4741 with the plasmids p426-GPD and p415-GPD.

Y0080 by transformation of BY4741 with the plasmids p416-TEF and p415-GPD.

Y0081 by transformation of BY4741 with the plasmids p426-TEF and p415-GPD.

Example 19

Propagation of *S. cerevisiae* Strains Expressing *S. bicolor* CYP79A1, CYP71E1 and UGT85B1 and of Strains Containing Mock Plasmids The above mentioned yeast strains were propagated in appropriate synthetic growth omission media lacking the same amino acids as used for selection of transformed cells. Cells were grown at 28° C., 175 RPM in a volume of 3 ml, until stationary phase. Liquid propagation was performed in 15 ml culture tubes.

Prior to glucose fermentation, the cells of the outgrown cultures were recovered by centrifugation (4000 RPM for ten minutes), separated from the spent media, washed once in synthetic glucose minimal (SD+) drop in media (see below), again recovered by centrifugation and finally resuspended in 3 ml of appropriated SD+ media.

Strains originally selected on SC-His, Ura, Leu were resuspended in SD+ Lys, Met. Strains originally selected on SC-His, Ura were resuspended in SD+ Lys, Met, Leu. Strains originally selected on SC-Ura, Leu were resuspended in SD+ Lys, Met, His.

After resuspension of cells in SD+ media, liquid cultures were kept at 28° C., 175 RPM and samples were collected, as described below, for subsequent LC-MS analysis.

Example 20

Metabolite Analysis of *S. cerevisiae* Strains Expressing *S. bicolor* CYP79A1, CYP71E1 and UGT85B1 and of Strains Containing Mock Plasmids In order to analyze the composition of secondary metabolites produced by the above mentioned yeast strains, samples of 0.5 ml were collected at the following time points after resuspension in SD+ media: 24 hours, 48 hours, 72 hours and 92 hours. In the case of analysis for dhurrin, only the time points of 24 and 48 hours were collected.

Samples to be analyzed for total content of a given secondary metabolite (amount of glycosylated and non-glycosylated molecules) will be treated with β-glucosidase (Fluka) prior to LC-MS.

Cells were separated from media by centrifugation (4000 RPM for ten minutes). 333 µl of the liquid phase from each sample was dried down in vacua, and resuspended in 50 µl of 50% MeOH. After centrifugation, at 15000 RPM for ten minutes of the MeOH resuspension, 25 µl was used for characterization by LC-MS. Samples were stored at −20° C. prior to LC/MS analysis.

Appropriate reference samples were manufactured by adding known amounts of the given reference compound to 0.5 ml of media (sampled 48 hours after resuspension in SD+ media) obtained from the corresponding yeast strain carrying mock plasmids. After adding the reference compound to media the reference samples were treated as described immediately above. In order to be able to quantify the amount of a given secondary metabolite, the corresponding reference samples were manufactured in triplicate, varying only in concentration of the reference compound (0.1 µg/ml, 1 µg/ml and 10 µg/ml). Finally, in order to uniquely identify the retention time for each particular molecule searched for, one reference sample containing only the given compound was prepared (1 µg/ml in 50% MeOH).

Analytical LC-MS was carried out using an Agilent 1100 Series LC (Agilent Technologies, Germany) coupled to a Bruker Esquire 3000+ ion trap mass spectrometer (Bruker Daltonics, Bremen, Germany). An XTerra MS C18 column (Waters, Milford, Mass., 3.5 µM, 2.1×100 mm) was used at a flow rate of 0.2 mL min$^{-1}$. The mobile phases were: A, 0.1% (v/v) HCOOH and 50 µM NaCl; B, 0.1% (v/v) HCOOH and 80% (v/v) MeCN. The gradient program was: 0 to 3 min, isocratic 3% (v/v) B; 2 to 30 min, linear gradient 3 to 50% B; 30 to 35 min, linear gradient 50% to 100% (v/v) B; 35 to 40 min, isocratic 100% B. The mass spectrometer was configured for electrospray ionization (ESI) in positive ion mode. Total ion current and ion traces for specific [M+Na]+ adduct ions were used for locating compounds. In the case of aglycone detection the mass spectrometer was configured for Atmospheric Pressure Chemical Ionization (APCI) in positive ion mode. Spectra were analyzed using Bruker Daltonics Dataanalysis v. 3.1 software (Bruker Daltonik, GmBH)

Quantification of a given secondary metabolite (aglycone or glycosylated version thereof) was done by integration of the area of the mass peak (LC-MS) and comparing obtained values to that of the standard curve from the three corresponding reference samples spiked with known amounts of that particular substance in question.

Example 21

Production of p-Hydroxymandelonitrile-β-D-Glucoside (Dhurrin) by Glucose Fermentation of S. cerevisiae Strains Expressing S. bicolor CYP79A1, CYP71E1 and UGT85B1.

The amount of Dhurrin produced by the yeast strains Y0109, Y0113, Y0117 and Y0121 was measured at the following time points. Quantification of Dhurrin was done by regression according to the equation [Dhurrin (ng/ml)]=6E-17$I^{2,5218}$ (R=0.92) were I is the area of the mass peak. This equation was derived from three spiked samples as described above.

TABLE 21.1

Dhurrin produced in S. cerevisiae strains expressing S. bicolor CYP79A1, CYP71E1 and UGT85B1.

| | Strain | | | |
|---|---|---|---|---|
| Time-point | Y0109 ng/ml | Y0113 ng/ml | Y0117 ng/ml | Y0121 ng/ml |
| 24 hours | 22.7 | 562 | 90.6 | 0.10 |
| 48 hours | 57.7 | 945 | 356 | 0.06 |

Retention time for Dhurrin (m/z = 334) was 13.6 minutes.

Tracer experiments by use of radio-labeled tyrosine demonstrated that the aglucone of dhurrin (p-hydroxymandelonitrile) was not present. It is accordance with prior art knowledge that explains that the aglucone of dhurrin is highly unstable in aqueous solutions (Halkier and Møller, 1989, Plant Journal 90: 1552-1559). The glycosylation performed by UGT85B1 results in a virtual unlimited overproduction of this unstable aromatic nitrile. No peak of m/z=334 at 13.6 minutes, exceeding the background noise was found in the case of yeast strains carrying mock plasmids (strains Y0084, Y0085, Y0086 and Y0087). In the case of strains (Y0094, Y0095, Y0096 and Y0097) carrying expression plasmids of CYP79A1 together with CYP71E1 no peak of m/z=334 at 13.6 minutes exceeding 10 ng/ml was found at any time point. Therefore the 945 ng/ml of Dhurrin found in the case of strain Y0113 after 48 hours of fermentation amounts to a least 94-fold overproduction, as a result of the expression of the glucosyltransferase UGT85B1.

Example 22

Production of Compounds Derived from the Dhurrin Biosynthesis Pathway by Expression of S. bicolor CYP79A1, CYP71E1 and UGT85B1.

Mass spectra from samples derived from strains expressing S. bicolor CYP79A1, CYP71A1 and UGT85B1 in non-equimolar amounts of gene products displays production of glucosylated molecules derived from intermediates of the Dhurrin biosynthesis pathway. It is therefore believed that glycosylation mediated by glycosyltransferases (here UGT85B1 as an example) can result in the continuous removal of intermediates from biosynthesis pathways thereby archieving overproduction of a given aglycone. In Table 22.1 the amounts of various putatively assigned glucosylated compounds derived from the Dhurrin biosynthesis pathway are listed. Quantification was performed similarly to that of the Dhurrin measurements described above, using the same equation.

TABLE 22.1

Glucosylated compounds, other than Dhurrin produced in S. cerevisiae strains expressing S. bicolor CYP79A1, CYP71E1 and UGT85B1.

| | Strain | | | | | | | | | | | |
|---|---|---|---|---|---|---|---|---|---|---|---|---|
| | Y0109 | Y0113 | Y0117 | Y0121 | Y0109 | Y0113 | Y0117 | Y0121 | Y0109 | Y0113 | Y0117 | Y0121 |
| | ng/ml | | | | ng/ml | | | | ng/ml | | | |
| Time point | p-glucosyloxy-phenylethanol[a] m/z = 323 | | | | p-glucosyloxy-phenylacetonitrile m/z = 318 | | | | p-glucosyloxy-benzaldehyde m/z = 307 | | | |
| 24 hours | 361 | 226 | 165 | 408 | 4.2 | 4.7 | 1.7 | 6.0 | 2.3 | 0.7 | 1.5 | 0.4 |
| 48 hours | 2606 | 1134 | 1830 | 2759 | 52 | 38 | 98 | 84 | 22 | 5.9 | 7.8 | 3.2 |
| 72 hours | 6424 | 3125 | 1649 | 12497 | 269 | 118 | 74 | 371 | 65 | 32 | 16 | 18 |
| 96 hours | 4979 | 4407 | 2952 | 15428 | 288 | 198 | 151 | 784 | 62 | 31 | 22 | 23 |

[a] Alternatively the m/z = 323 ion corresponds to p-glucosyloxy-benzoic acid or glucosyl p-hydroxybenzoate. Retention time of p-glucosyloxy-phenylethanol was 14.4 minutes. Retention time of p-glucosyloxy-phenylacetonitrile was 14.4 minutes. Retention time of p-glucosyloxy-benzaldehyde was 19.7 minutes.

Example 23

Overproduction of Compounds Derived from Intermediates of the Dhurrin Biosynthesis Pathway by Expression of the S. Bicolor Genes CYP79A1, CYP71A1 and UGT85B1 in S. cerevisiae.

Unambiguous identification of the above mentioned glucosides are achieved similarly to the method described for dhurrin identification using authentic standards for p-glucosyloxy-phenylethanol, p-glucosyloxy-benzoic acid, glucosyl p-hydroxybenzoate, p-glucosyloxy-phenylacetonitrile and p-glucosyloxy-benzaldehyde.

Identification and quantification of aglycone molecules are performed in the following way: growth media from strains expressing the Dhurrin biosynthesis genes or from strains carrying mock plasmids are collected at the same time points and by the same methods as described above. Thereafter the spent media are treated with β-glucosidase (to release the aglycones from theirs glycoside forms). Again, in order to be able to quantify the amount of a given aglycone, the corresponding reference samples are manufactured in triplicate, varying only in concentration of the reference compound (0.1 µg/ml, 1 µg/ml and 10 µg/ml). Finally, in order to uniquely identifying the retention time for each particular molecule searched for, one of each reference sample containing only the given compound is prepared (1 µg/ml in 50% MeOH).

Demonstration of overproduction by glucosylation is done by comparison of the produced amount of the given aglucone (after β-glucosidase treatment) from strains expressing UGT85B1 together with CYP79A1 (and in some cases also CYP71E1) to that of strains expressing only CYP79A1 (and in some cases also CYP71E1). This procedure demonstrates at least 1.5 times overproduction.

REFERENCES

The references mentioned below are a selection of the references that are considered most pertinent with respect to the present invention.

Paquette, S. et al, Phytochemistry 62 (2003) 399-413.
WO01/07631.
WO01/40491
Arend, J et al., Biotech. & Bioeng (2001) 78:126-131
Tattersall, D B et al, Science (2001) 293:1826-8
Moehs, C P et al, Plant Journal (1997) 11:227-236
U.S. Pat. No. 6,372,461

The invention claimed is:

1. A method of producing a low molecular weight organic aglycon compound comprising following steps:
   a) fermenting a microorganism cell in a suitable medium where the microorganism is capable of growing, the microorganism comprising:
      a gene encoding a product involved in the biosynthesis pathway leading to a low molecular weight organic aglycon compound; and,
      a glycosyltransferase gene encoding a glycosyltransferase capable of glycosylating the produced aglycon;
      wherein the cell produces the aglycon, the glycolsyltransferase and, by interaction of gylcosyltransferase with aglycon, the cell also produces the corresponding glycosylated form of the aglycon;
   b) deglycosylating the glycosylated form of the aglycon; and
   c) recovering the aglycon compound; (i) wherein the low molecular weight organic aglycon compound has a molecular weight from 50 to 3000, and (ii) wherein the glycosyltransferase is a glycosyltransferase capable of conjugating a sugar to the aglycon compound; and
   wherein the microorganism cell is a yeast cell; and
   wherein the low molecular weight organic aglycon compound is vanillin.

2. The method of claim 1, wherein the yeast cell with the glycosyltransferase during culture fermentation is capable of producing higher amounts of the glycosylated form of the vanillin as compared to the amounts of the corresponding vanillin produced by the same yeast cell without the glycosyltransferase.

3. The method of claim 1, wherein the yeast cell is a yeast cell selected from the group consisting of *Saccharomyces spp* and *Pichia spp*.

4. The method of claim 1, wherein the glycosyltransferase gene is a heterologous glycosyltransferase gene.

5. The method of claim 1, wherein the glycosyltransferase is an UDPG-glycosyltransferase or an UDPG-glucosyltransferase.

6. The method of claim 1, wherein the deglycosylating step b) of claim 1 takes place outside the growing cell following excretion or extraction of the glycosylated form of the vanillin produced in step a).

7. The method of claim 6, wherein the deglycosylating step b) is an enzymatic process mediated by a beta-glucosidase.

* * * * *